United States Patent [19]

Pioch

[11] Patent Number: 4,468,399

[45] Date of Patent: Aug. 28, 1984

[54] 2-[2-(2-AMINOALKYL-4-THIAZOLYLMETHYLTHIO)ALKYL]-AMINO-5-SUBSTITUTED-4-PYRIMIDONES

[75] Inventor: Richard P. Pioch, Indianapolis, Ind.

[73] Assignee: Eli Lilly and Company, Indianapolis, Ind.

[21] Appl. No.: 515,726

[22] Filed: Jul. 20, 1983

Related U.S. Application Data

[63] Continuation-in-part of Ser. No. 334,784, Dec. 28, 1981, abandoned.

[51] Int. Cl.$^3$ .................. C07D 417/12; C07D 417/06; C07D 417/14; A61K 31/505
[52] U.S. Cl. .............................. 424/251; 424/248.4; 544/123; 544/320; 544/321; 548/203; 548/205
[58] Field of Search ..................... 424/251, 248.4; 544/320, 321, 123

[56] References Cited

FOREIGN PATENT DOCUMENTS 83186 7/1983 European Pat. Off. ............ 424/251

*Primary Examiner*—Robert Gerstl
*Attorney, Agent, or Firm*—James L. Rowe; Arthur R. Whale

[57] ABSTRACT

2-[2-(2-aminoalkyl-4-thiazolylmethylthio)-alkylene]amino-5-aromatic-substituted alkylene-4-pyrimidones and related compounds, $H_2$ receptor antagonists, useful in inhibiting gastric acid secretion in mammals.

54 Claims, No Drawings

2-[2-(2-AMINOALKYL-4-THIAZOLYLMETHYL-THIO)ALKYL]-AMINO-5-SUBSTITUTED-4-PYRIMIDONES

CROSS-REFERENCE

This is a continuation-in-part application of my co-pending application Ser. No. 334,784, filed Dec. 28, 1981, now abandoned.

BACKGROUND OF THE INVENTION

Over the past few years, several research groups in, chiefly, England or the United States of America, have synthesized histamine $H_2$-receptor antagonists useful in treating peptic ulcers. Broadly speaking, these compounds can be classed as substituted amidines; e.g., acetamidine,

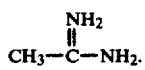

Related compounds include guanidines,

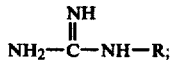

mercaptoamidines or isothioureas,

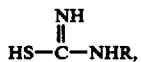

tautomeric with the thioureas

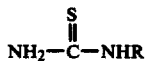

and ethenediamines,

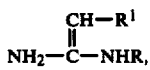

tautomeric with

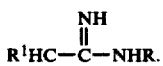

In these new $H_2$-receptor antagonists, the amidine usually occurs at one end of a bridging group; i.e., —CH$_2$—Y—(CH$_2$)$_2$—where Y is S, O, NH or CH$_2$. The other end of the bridging group has usually been an aromatic heterocycle, most frequently imidazole. The heterocyclic ring can be substituted.

The first drug recognized as a powerful $H_2$-receptor antagonist was a thiourea, burimamide—N-methyl-N′-(4-[4(5)-imidazolyl)]butyl)thiourea—having the following formula:

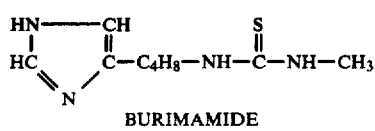

BURIMAMIDE

The pharmacological properties of this compound are disclosed in *The Pharmacological Basis of Therapeutics*, Goodman & Gilman 5th Ed. (MacMillan Publishing Co., Inc., New York) page 612. Burimamide was developed by a group of research workers headed by Black and Durant.

A second generation of histamine $H_2$-receptor atagonists comprised compounds developed by Black, Durant and co-workers with a structure more or less similar to that of burimamide, but in which there was a permissible interrupting group—oxygen, sulfur or NH—in the alkyl side chain attached to the hetero ring. The most prominent of this group of compounds has been cimetidine, chemically N-cyano-N′-methyl-N″-[2-([(5-methyl-1H-imidazol-4-yl)methyl]thio)ethyl]guanidine, represented by the formula below:

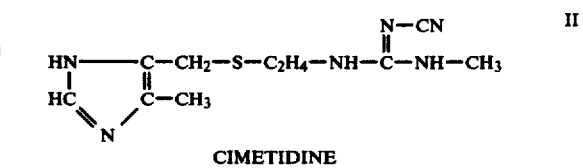

CIMETIDINE

A large number of patents based upon several original filings Ser. Nos. 230,451; 284,992; 385,027; 481,716; 816,420; 436,285; 542,971; 468,617; 384,993; and 385,027) have issued to Durant et al including, but not limited to, the following U.S. Pat. Nos. 3,950,333; 4,049,672; 4,022,797; 4,137,237; 4,024,271; 4,070,475; 4,154,844; 3,905,984; 4,027,026; 3,932,427; 4,018,928; 3,950,353; 4,053,473; 4,018,931; 4,069,327; 4,151,288; 4,000,296; 4,083,988; 4,129,657; 4,098,898; 4,166,856; 4,072,748; 3,971,786; 4,060,620; 3,876,647; 3,920,822; 3,897,444; 3,975,530; 4,226,874; 4,228,291; 4,230,865 and 4,221,802.

Other disclosed hereto ring systems in addition to imidazole include pyrazole, pyridine, pyrimidine, pyridazine, thiazole, isothiazole, oxazole, isoxazole, triazole, thiadiazole, benzimidazole and tetrahydroimidazo[1,5-a]pyridine, but the greatest emphasis has continued to be placed on compounds having an imidazole ring system. Groupings which may be present at the terminal end of the alkyl or alkylthioalkyl bridging group include, among others, guanidine, cyanoguanidine, urea, nitroethenediamine and thiourea.

Patents referring to thiazole or oxazole ring systems are of particular relevance to this invention. The two basic disclosures by the Durant group are contained in U.S. Pat. Nos. 3,950,333 and 3,950,353, both of which are continuations-in-part of Ser. No. 290,584 which was in turn a continuation-in-part of Ser. No. 230,451. In U.S. Pat. No. 3,950,333, the disclosure relating to thiazoles begins at Example 115, column 37. Thiazoles substituted with a chloro or an alkyl group are described. The thiazole nucleus is then attached at the 2- or 4-position of the thiazole ring to an alkylthioalkyl side chain terminating in an N-cyano-N′-methylguanidine. This disclosure is followed by similar disclosures for isothiazoles, oxazoles and isoxazoles. The disclosure in U.S. Pat. No. 3,950,353 relating to thiazoles begins at Example 110, column 37. Here, substantially the same thiazole nucleus is attached via a bridging group to an N-methylthiourea. A similar disclosure is present for isothiazoles, oxazoles and isoxazoles. U.S. Pat. No. 4,022,797, a division, specifically claims the cyanoguanidine derivatives and U.S. Pat. No. 4,137,234, another division, specifically claims thioureas.

U.S. Pat. No. 4,000,296 discloses and claims a group of N-alkyl or N-arylsulfonyl-N'-alkyl-N"(heterocyclealkylthioalkyl)guanidines in which the heterocycle can be thiazole, isothiazole, oxazole or isoxazole. Alkyl, alkylaminoalkyl and alkyloxyalkyl bridging groups (connecting the heterocycle to the substituted guanidine group) are also disclosed. Substituted heterocycles belonging to any of the above classes are not disclosed. U.S. Pat. No. 4,166,856, originating with the Durant group, discloses and claims a number of imidazoles and thiazoles carrying the usual alkylthioalkyl-guanidine, -thiourea or -ethenediamine side chain, which side chain is invariably attached at the 2-position of the heterocyclic ring.

Another group of investigators under Yellin has disclosed—see U.S. Pat. Nos. 4,165,377, 4,234,735 and 4,165,378—certain novel thiazoles having a side chain such as those discussed above attached at the 4-position of the thiazole ring; i.e., an alkylthioalkyl-guanidine, -ethenediamine or -thiourea group attached thereto, but also bearing a guanidino group in the 2-position of the thiazole. Alkylene, alkenylene and alkyloxyalkyl bridging groups are also disclosed. A representative compound is 2-guanidino-4-[2-(2-cyano-3-methylguanidino)ethylthiomethyl]thiazole which is said to have greatly increased activity over cimetidine.

A third research group at Allen and Hanburys Ltd. has prepared compounds with a furan ring carrying the standard alkylthioalkyl (or alkyloxyalkyl or alkyl) side chain terminating in a substituted guanidine or ethenediamine group, and also having a dialkylaminoalkyl substituent attached at a second position in the furan ring—see U.S. Pat. Nos. 4,128,658 and 4,168,855. Belgian Pat. Nos. 867,105 and 867,106 disclose the corresponding thiophene and aminoalkylbenzenes. Several of the compounds thus produced have a greater $H_2$-receptor antagonist activity than cimetidine. The most prominent of these new compounds is ranitidine:

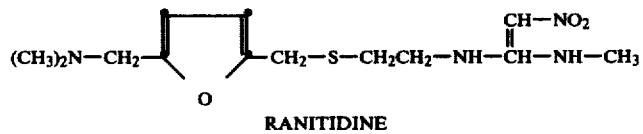

RANITIDINE

U.S. Pat. No. 4,233,302 from Glaxo also discloses a group of $H_2$-receptor antagonists having a dialkylamino alkyl substituted thiophene or furan as one portion of the molecule.

Finally, a research group at Bristol-Myers have issued several United States patents involving different heterocycles. The first of these, U.S. Pat. No. 4,203,909, relates to furans carrying an alkylthioalkyl-guanidine (or thiourea or ethenediamine) side chain in the 2-position, an aminoalkyl side chain in the 5-position and an alkynylamino group as part of the terminal portion of the molecule. One of the compounds, 1-nitro-2-(2-propynylamino)-2-(2-[(5-dimethylaminomethyl-2-furyl)methylthio]ethylamino)ethylene, is said to have 7.45 times the activity of cimetidine in a standard $H_2$-receptor assay. A second patent, U.S. Pat. No. 4,200,578, covers broadly thiazoles substituted with an alkylthioalkyl-guanidine (or thiourea or ethenediamine) side chain, and again carrying an obligatory alkynyl group in the terminal portion. Other permissible substituents in the thiazole ring include alkyl, guanidino or aminoalkyl.

Recently, Netherlands patent application 8004967, to Bristol-Myers published Sept. 1, 1980, same as U.K. Pat. No. 2,067,987, discloses a new and different and group, a 1,2,5-thiadiazole-1-oxide attached by a conventional bridging group to any of a number of hetero rings:

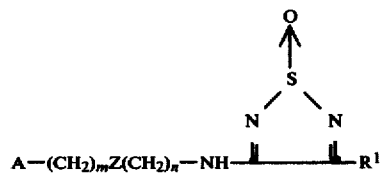

wherein A can be phenyl, imidazolyl, furyl, thenyl, thiazolyl, etc substituted by a guanidino group or a dialkylaminoalkyl group. 2-[2-(dimethylaminomethyl)-4-thiazolylmethylmercapto]ethylamine is specifically disclosed in Example 22. The same intermediate is disclosed by my copending application Ser. No. 193,192 filed Oct. 2, 1980 now U.S. Pat. No. 4,375,547.

More recently in the $H_2$-receptor antagonist art, there has been disclosed a new type of terminal group, a 4-pyrimidone group,

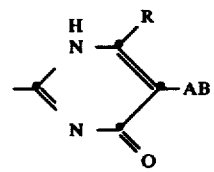

to replace the cyanoguanidine or nitroethenediamine terminal group. This new group, when taken with the amino group terminating the bridging group, can be looked upon as a "ring-closed" guanidine with the imino group linked to the second amino group by a 3carbon fragment. For example, U.S. Pat. No. 4,255,428 discloses compounds of the formula:

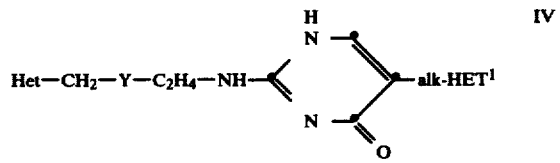

where Het can be a 2-thiazolyl radical (not substituted), Y is S or $CH_2$ and Het[1] is an hydroxypyridyl radical. Derwent Abstract 19764 D/12 discloses substituted pyrimidones attached by the conventional side chain to a N-containing heterocyclic ring which can be substituted with, among other groups, an amino group. Derwent Abstract 20656 D/12 discloses similar compounds in which the hetero ring can be a dialkylaminoalkyl substituted thiadiazole as do U.S. Pat. No. 4,234,585, and Belgian Pat. No. 877,889 wherein the heterocycle is a thiophene or furan permissibly substituted with a dialkylaminoalkyl group. A group of patents: U.S. Pat. Nos. 4,154,834 and 4,216,318 and South African Pat. Nos. 79/1617 and 79/1943 disclose compounds according to formula IV in which Het is an unsubstituted 2-thiazolyl group and Het¹ can be, in one reference, a 3-pyridyl radical among a myriad of other aromatic groups. Finally, EPO Pat. No. 11728 discloses compounds according to formula IV in which Het is a 4-thiazolyl radical but in which there is a mandatory 2-guanidino group in the thiazole ring.

SUMMARY OF THE INVENTION

This invention provides compounds of the formula

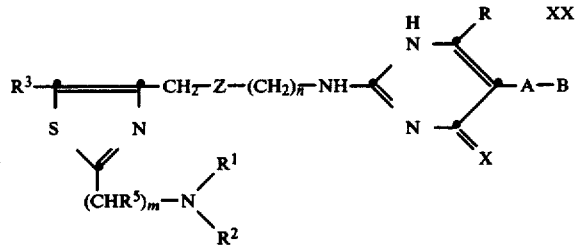

wherein each of R, R¹, R² and R³ are individually H or (C₁-C₃) alkyl, one of R¹ and R² can be benzyl or benzoyl, and, when taken together with the nitrogen to which they are attached, R¹ and R² represent a saturated 5-7 member heterocyclic ring containing permissibly a second hetero atom selected from the group O and N such as piperidino, pyrrolidino or morpholino; except that only one of R¹ and R² can be H when Z is CH₂;

X is S or O;
Z is O, S or CH₂;
n is 2 or 3 when Z is O or S and n is 1, 2 or 3 when Z is CH₂;
R⁵ is H or CH₃;
m is 1, 2 or 3;
A is (C₁-C₅) alkylene or (CH₂)$_q$X(CH₂)$_p$ wherein q and p are individually 0, 1, 2 or 3 and the sum of q plus p is 0-4, and
B is H, CH₃, (C₃-C₆) cycloalkyl, imidazolyl, thiazolyl, pyridyl, (C₁-C₃)alkylpyridyl, di(C₁-C₃)alkylpyridyl, hydroxypyridyl, (C₁-C₃)alkyloxypyridyl, furyl, thienyl, naphthyl, 5-(1,3-benzodioxolyl), 6-(2,3-dihydro-1,4-benzodioxinyl) tetrahydrofuryl, or phenyl permissibly substituted with 1 or 2 (same or different) (C₁-C₃) alkyl, (C₁-C₃) alkyloxy, methylene dioxy, halo, OH, benzyloxy, CF₃, (C₁-C₃)alkyl-O-(C₁-C₃)alkylene, di(C₁-C₃)alkylamino(C₁-C₃)alkylene.

A preferred group of histamine H₂ receptor antagonists coming within the scope of formula XX are the following:

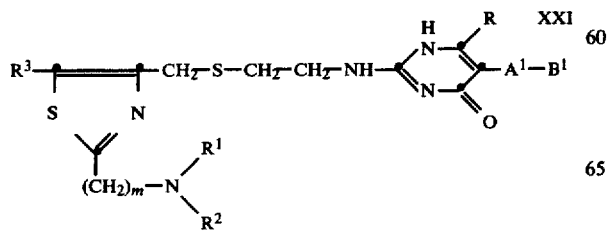

wherein R, R¹, R² and R³ are H or (C₁-C₃) alkyl, R¹ is benzyl when R² is (C₁-C₃)alkyl, m is 1-3, A¹ is a (C₁-C₅) alkylene bridging group and B¹ is pyridyl, phenyl, 5-(1,3-benzodioxolyl), 6-(2,3-dihydro-1,4-benzodioxinyl), (C₁-C₃)alkylpyridyl, di(C₁-C₃)alkylpyridyl, (C₁-C₃)alkyloxypyridyl or hydroxypyridyl.

In the above formulas, XX and XXI, the 4-pyrimidone or 4-pyrimidinethione ring has been written with the following structure (A):

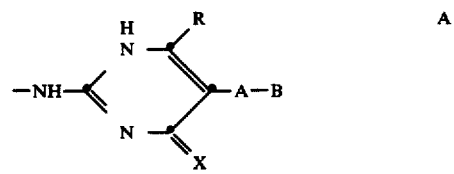

It should be recognized, however, that this structure is tautomeric with the following structures (B and C):

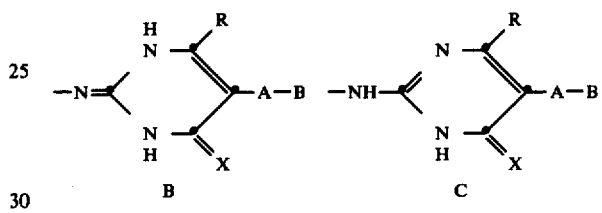

Formulas XX and XXI above include all such tautomeric structures within their scope and thus within the scope of my invention. All three tautomeric forms are disclosed by implication whenever any single one of the tautomers is drawn and it should be understood that all such tautomeric equivalents are embraced by the present invention. Compounds according to structure A would be named systematically as 4(1H)-pyrimidones, those according to structure B as 4(1,3H)-pyrimidones, and those according to structure C as 4(3H)-pyrimidones. Again, regardless of which tautomer name is used to describe a given compound, the other tautomers are included within that name as forming part of my invention.

In like fashion, the pyrimidine rings below enjoy enol-keto tautomerism

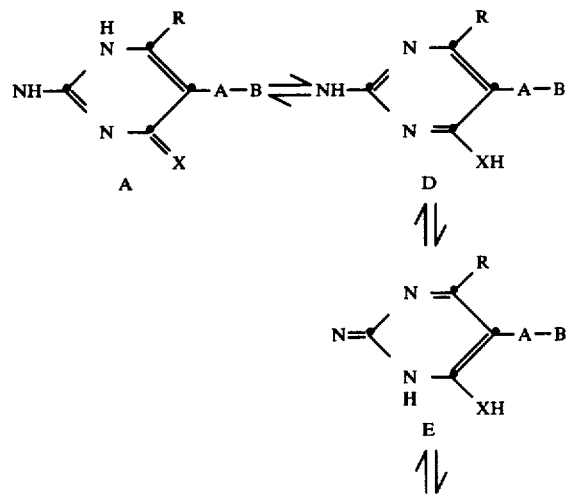

-continued

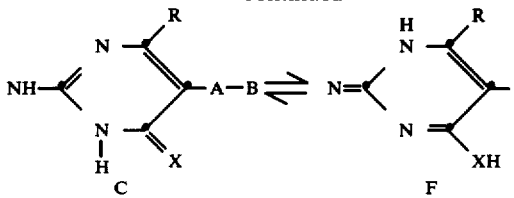

with a mono hydroxy or mercaptopyrimidine. Again, such tautomeric forms are included within the scope of Formulas XX and XXI and are therefore part of my invention.

Studies of 4-pyrimidinone tautomerism indicate that structures A and C exist in approximately equal amounts, and that structure B is formed where the substituent at C-2 is an electron withdrawing group. Otherwise the oxo forms (A, B, C) predominate over the enol forms (D, E, F).

Bases falling within the scope of the above formula include:

2-(2-[2-(diethylaminomethyl)-4-thiazolylmethyloxy]ethylamino)-5-(2-imidazolyl)methyl-4-pyrimidone.

2-[3-(2-[3-(dimethylamino)propyl]-4-thiazolylmethylthio)propylamino]-5-[3-(2-thiazolyl)propyl]-6-ethyl-4-pyrimidone 2-[2-(2-[2-dimethylamino)ethyl-4-thiazolylmethylthio)ethylamino]-5-(2-furyl)ethyl)-4-pyrimidinethione;

2-(2-[2-(dimethylaminomethyl)-4-thiazolylmethylthio]ethylamino)-5-(4-thiazolyl)methyl-4-pyrimidone 2-[3-(2-dimethylaminomethyl-4-thiazolylmethylthio)-propylamino]-5-(4-thiazolyl)methyl-4-pyrimidone.

2-[5-(2-dimethylaminomethyl-4-thiazolyl)pentylamino]-5-(2-thienyl)methyl-6-methyl-4-pyrimidone;

2-(2-[2-(2-dimethylamino-2-methylethyl)-4-thiazolylmethylthio]ethylamino)-5-(2-imidazolyl)methyl-4-pyrimidinethione;

2-(2-[2-(1-dimethylamino-1-methylethyl)-4-thiazolylmethyloxy]ethylamino)-5-(3-thienyl)methyl-6-ethyl-4-pyrimidone;

2-(2-[2-(1-dimethylaminoethyl)-4-thiazolylmethyl]ethylamino)-5-[2-(2-thiazolyl)ethyl]-4-pyrimidone.

2-[2-(2-diethylaminoethyl)-4-thiazolylmethylthio]ethyl-5-(4-methyl-2-pyridyl)methyl-6-ethyl-4-pyrimidone;

2-[3-(2-di-n-propylaminomethyl-4-thiazolylmethylthio)propylamino]-5-[2-(2-pyridyl)ethyl]-4-pyrimidone;

2-[4-(2-[3-(methylamino)propyl]-4-thiazolyl)-butylamino]-6-methyl-5-(2-thiazolyl)methylthiomethyl-4-pyrimidone;

2-[2-(2-diethylaminomethyl-5-methyl-4-thiazolylmethyloxy)ethylamino]-5-(2-pyridyl)methoxymethyl-4-pyrimidone;

2-(3-[2-(2-dimethylaminoethyl)-4-thiazolyl]-propylamino)-5-[2-(3-pyridyl)-2-methylethyl]-4-pyrimidone;

2-[2-(2-methylaminomethyl-5-ethyl-4-thiazolylmethylthio)ethylamino]-5-(2-furyl)methyl-4-pyrimidone;

2-(2-[2-(2-aminoethyl)-4-thiazolylmethylthio]ethylamino)-5-(α-naphthyl)methyl-4-pyrimidone;

2-[2-(3-aminopropyl-4-thiazolylmethyloxy)ethylamino]-5-(2-thienyl)methyl-4-pyrimidone;

2-[2-(2-diethylaminomethyl-4-thiazolylmethyloxy)ethylamino]-5-[3-(4,6-dimethyl-2-pyridyl)]propyl-6-ethyl-4-pyrimidone;

2-(3-[2-(3-methylaminopropyl)-4-thiazolyl]propylamino)-5-(2-(2,4-dichloro)phenyl)ethyl-4-pyrimidone;

2-[4-(2-dimethylaminomethyl-4-thiazolyl)-butylamino]-5-(3-pyridyl)-4-pyrimidone;

2-(5-[2-(2-dimethylamino-2-methylethyl)-4-thiazolyl]pentylamino)-5-(p-tolyl)methyl-6-n-propyl-4-pyrimidinethione;

2-(3-[2-(3-diethylaminopropyl)-4-thiazolylmethylthio]propylamino)-5-[2-(2,3-methylenedioxyphenyl)ethyl]-4-pyrimidone, and the like.

In Formula XX, the term ($C_1$–$C_3$) alkyl includes methyl, ethyl, n-propyl or isopropyl. Thus, the term ($C_1$–$C_3$)alkylphenyl would include o, m and p-tolyl, o, m, and p-ethylphenyl and the like. Similarly, the term ($C_1$–$C_3$)alkoxyphenyl includes o, m, and p-anisyl, o, m, and p-ethoxyphenyl and the like. The term halophenyl includes o, m, and p-chlorophenyl, bromophenyl, fluorophenyl and iodophenyl. Disubstituted phenyls such as 2,4-xylyl, 3,4-dichlorophenyl, 2-methyl-4-chlorophenyl, 3,4-dihydroxyphenyl and the like are also included within the scope of the term "substituted phenyl".

The term ($C_3$–$C_6$) cycloalkyl includes cyclopropyl, cyclobutyl, cyclopentyl, cyclohexyl, methylcyclopentyl (all isomers), methylcyclobutyl, dimethylcyclobutyl and the like.

B in the above formula represents both heteroaryl groups and hydrocarbyl aromatic groups. The various heteroaryl groups which B can represent include illustratively 2-, 3- and 4-pyridyl, 2- or 3-thienyl or furyl, 2- or 4-imidazolyl, and 2- or 4-thiazolyl.

When B is substituted pyridyl, the alkyl, alkoxy or hydroxy substituents may occupy any otherwise unoccupied portions in those rings. Likewise, when B is a substituted phenyl group, the one or two substituents may occupy any of the open positions in the benzene ring.

A preferred group of radicals which B can represent includes 2,3 and 4-pyridyl substituted with one or two methyl, methoxy or hydroxy groups such as 2-pyridyl, 3-pyridyl, 4-pyridyl, 6-methyl-3-pyridyl, 5-methyl-3-pyridyl, 6-methoxy-3-pyridyl, 2-methyl-3-pyridyl, 2-methyl-4-pyridyl, 3-methoxy-4-pyridyl, 2-methoxy-4-pyridyl, and 5-(1,3-benzodioxolyl).

The pharmaceutically-acceptable acid addition salts of the compounds of this invention include salts derived from inorganic acids such as: hydrochloric acid, nitric acid, phosphoric acid, sulfuric acid, hydrobromic acid, hydriodic acid, phosphorous acid and the like, as well as salts derived from organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Compounds according to XX above can have three or more basic centers. These are a strongly basic amine group in the aminoalkyl group attached at position 2 of the thiazole ring, a less basic in the amine attached to the pyrimidone ring at C-2 and the basic ring nitrogen of the thiazole. A fourth basic group can also be present depending on the nature of the substituent "B"; for example, if B is pyridyl, the pyridyl nitrogen can form salts with strong acids. Thus, if a mineral acid is used, such as HCl or HBr, trihydrohalide salts can be prepared. Monohalide or dihalide salts are also preparable by titrating a solution of the base with acid and then evaporating the solution of the partially neutralized base to dryness. Weaker acids, such as some of the organic acids enumerated above, will form a salt only with the most basic center in the 2-dialkylaminoalkylthiazole.

The compounds of this invention wherein Z is S or O—in other words, a heteroatom—are conveniently prepared from a 2-[(2-aminoalkyl-4-thiazoly)methylheteroatom]alkyl amine. The preparation of these starting materials is illustrated in Flow Chart A below using a compound in which the heteroatom is sulfur for exemplary purposes only.

Flow Chart A

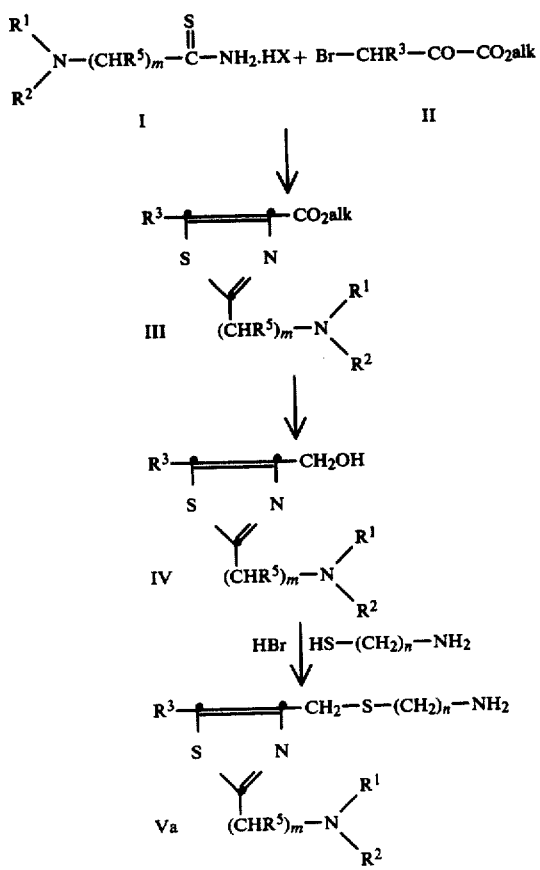

In the above Flow Chart, alk is conveniently methyl or ethyl and $R^1$, $R^2$, $R^3$, $R^5$, m and n have the same meaning as hereinabove.

In accordance with the above procedure, an acid addition salt of an aminoalkylthioacetamide (I) is reacted with a beta-bromo-alpha-ketoester (II) such as ethyl bromopyruvate ($R^3$=H) to yeild an alkyl (methyl or ethyl) 2-(aminoalkyl)-4-thiazolecarboxylate (III). Reduction of this ester with a suitable hydride reducing agent such as lithium triethylborohydride, lithium aluminumhydride, sodium borohydride, diisobutylaluminumhydride and the like yields the corresponding hydroxymethyl compound (IV). Reaction of the 4-hydroxymethylthiazole with cysteamine or its higher homologue 3-mercaptopropylamine in the presence of acid yields directly a (2-aminoalkyl-4-thiazolylmethylthio)alkylamine (Va) optionally substituted with an alkyl group in the 5-position of the thiazole ring.

In the process indicated in Flow Chart A, in going from IV to Va, the hydroxymethyl group can be halogenated as with thionylchloride to yield a 4-chloromethylthiazole and the chlorinated compound in turn reacted with the sodium salt of the particular mercaptoalkylamine. In fact, any standard leaving group (a group labile to nucleophilic displacement) can be employed here in place of chloro in the chloromethyl side chain including for example p-tosyloxy, mesyloxy (methanesulfonyloxy), bromo, iodo and the like.

Alternatively, the 4-chloromethylthiazole hydrochloride (or other suitable acid addition salt) can be fused with a mercaptoalkylamine salt such as a hydrochloride salt to yield the desired primary amine (Va—Z=S).

If it is desired to prepare the side chain oxygen analogue of Va (Z=O), a process utilizing 2-chloroethylamine or 3-chloropropylamine to react with the 4-thiazolemethanol, under basic conditions, can be employed as well as can the analogous Williamson ether process using the sodium salt of the hydroxyalkylamine with a 4-thiazolylmethyl halide.

The compounds of this invention can be prepared by reacting an amine of formula V with a pyrimidone carrying at C-2 a leaving group Q capable of undergoing nucleophilic displacement by a primary amine). Examples of such leaving groups include nitroamino, ($C_1$-$C_3$)alkylthio, aralkylthio such as benzylthio, halo such as Cl or Br, methylsulfinyl, toluenesulfonyloxy, mesyloxy, and the like. When Q is a nitroamino group a lower alkanol such as ethanol or acetonitrile can be used as the reaction solvent and it is necessary to heat the reaction mixture. In general, the reaction is affected at a temperature in the range 50°-150° C. The reflux temperature of the reaction mixture can conveniently be employed. When Q is ($C_1$-$C_3$)alkylthio, the reaction is carried out at an elevated temperature, with or without a solvent. However, if it is desired to use a solvent, DMSO, DMF, pyridine or alkyl substituted pyridines such as gamma-picoline are suitable for that purpose.

FLOW CHART B

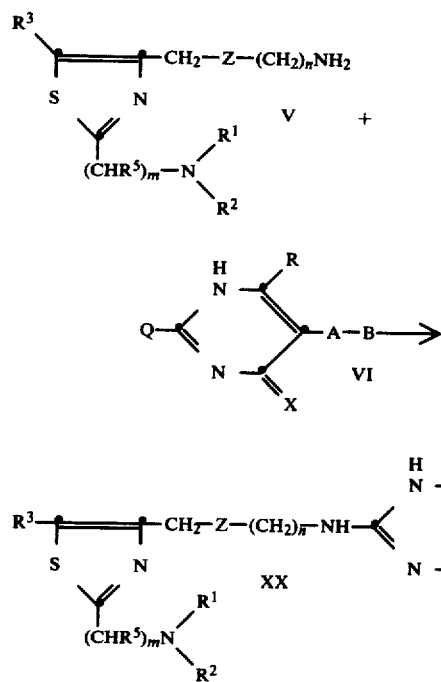

wherein R-R$^3$, R$^5$, n, m, x, Z, A and B have their previous significance and Q is a leaving group, except that R$^1$ and R$^2$ cannot both be H.

The preparation of amines of formula V is described in European Patent Specification No. 49,618 and the preparation of the pyrimidines of formula VI in, for instance, U.S. Pat. No. 4,216,318. Alternative processes are available for the preparation of the compounds of this invention. For example, the reaction scheme of Flow Chart B can be carried out with starting materials in which the roles are reversed; i.e., the leaving group is attached to the thiazole moiety and the reacting group (here OH or SH) is linked to the pyrimidone as the Flow Chart C.

FLOW CHART C

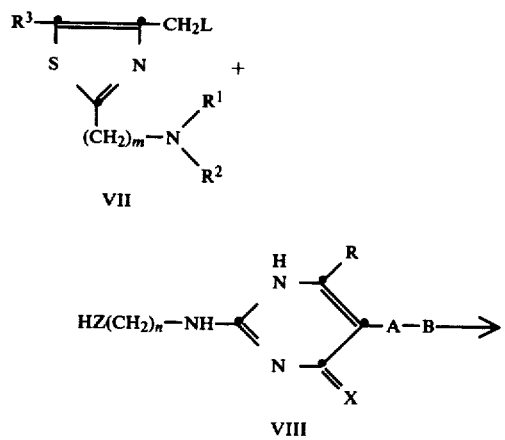

-continued
FLOW CHART C

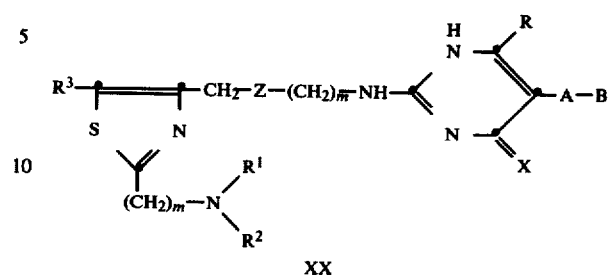

wherein R-R$^3$, R$^5$, Z, A, B, m and n have their previous significance and L is a leaving group such as OH, O-mesyl, O-tosyl, Cl, Br and the like. When L is OH, the reaction is carried out in the presence of a strong acid such as methanesulfonic acid of 12N hydrochloric acid. When L is a halogen (Cl or Br) or a halogen-like group (tosyloxy or mesyloxy), the reaction is carried out in the presence of a base such as the alkali metal (sodium) salt of a lower alkanol, and the same lower alkanol is conveniently used as a solvent. Optionally, when L is a halogen such as Cl or Br, the reaction can be carried out at an elevated temperature in the absence of a solvent by employing each reactant in the form of an acid addition salt, preferably as hydrochloride salts. It should be noted that the process of Flow Chart C cannot be used under acidic conditions if the group represented by "B" contains an ether function, such as a 6-methoxy-3-pyridyl group, since this ether group may be cleaved under the specified reaction conditions.

A second alternative synthetic procedure involves the reaction of N-2-(2-aminoalkyl-4-thiazolylmethylthio)ethylguanidine with a substituted α-acyl ester according to the Flow Chart D.

FLOW CHART D

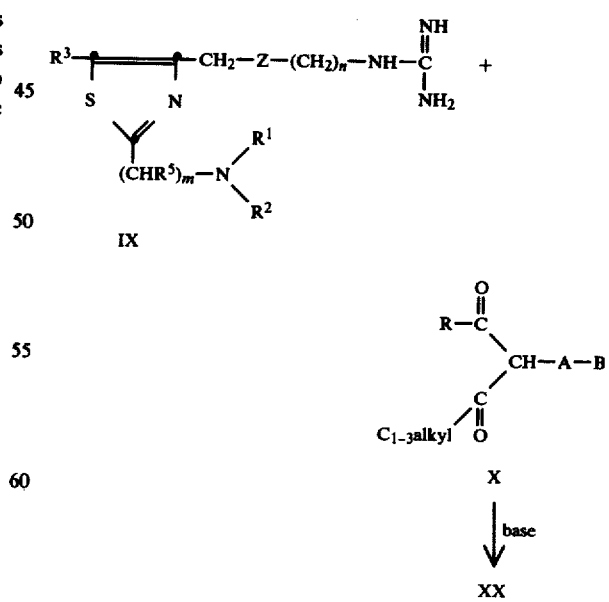

wherein R-R$^3$, R$^5$, m, n, A and B have their previous meanings and Z is S. A similar reaction will take place where Z is O or CH$_2$. The reaction of Flow Chart D is carried out by heating the reactants in a mutual solvent, conveniently a lower alkanol [(C$_1$-C$_3$)alkyl-OH] in which the (C$_1$-C$_3$) alkyl group is the same as that in the alkyl ester group of X and preferably in the presence of a base such as an alkali metal salt of the alkanol solvent. The N-2-(2-aminoalkyl-4-thiazolylthio)ethylguanidine (IX) can be prepared from the primary amine (V or Va) of Flow Chart A, with a salt of an alkylisothiourea

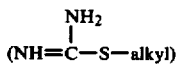

such as a methylisothiouronium salt where the alkylthio group is a leaving group. Alternatively, the product IX can be prepared by guanylating the primary amine (V) with, for example, cyanamide or 3,5-dimethylpyrazole-1-carboxamidine.

In Flow Chart B, the pyrimidone or pyrimidinethione reactant VI has the structure

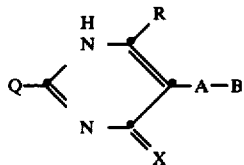

VI where Q is a leaving group such as nitroamino, (C$_1$-C$_3$)alkylthio, benzylthio, halo, methylsulfinyl, tosyloxy, mesyloxy, etc. The pyrimidones (X=O) are conveniently prepared by a reaction similar to the ring closure reaction of Flow Chart D optionally followed by an alkylation reaction. For example, the α-acyl ester (X) can be reacted with thiourea to yield a 2-mercapto-5-substituted-4-pyrimidone of the formula

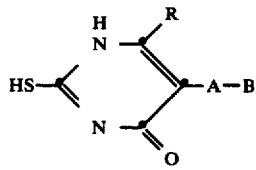

which intermediate can in turn be alkylated, as with an alkylhalide or dialkylsulfate, preferably in the presence of base to yield reactant VI of Flow Chart B wherein Q is a loweralkylthio [(C$_1$-C$_3$)S] leaving group. The same compound can be prepared directly by reaction of the α-acylester (X) with an S-alkylisothiouronium salt preferably in the presence of base. When it is desired to prepare a pyrimidone (VI) in which Q is nitroamino, the above α-acyl ester is reacted with nitroguanidine in the presence of base, preferably a lower alkoxide in a lower alkanol solvent where the lower alkyl groups are the same.

Compounds wherein X is S in VI in Flow Chart B are prepared by acylating a pyrimidone (VI where Z is O) with a dilower alkylthiocarbamoyl chloride

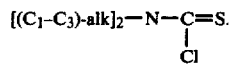

The O-dialkylthiocarbamate thus prepared is then thermally rearranged to yield the S-dialkylcarbamate. Hydrolysis yields the desired pyrimidinethione (VI where X is S).

The substituted pyrimidones starting materials (VIII) of Flow Chart C are prepared from VI according to the following reaction scheme.

FLOW CHART E

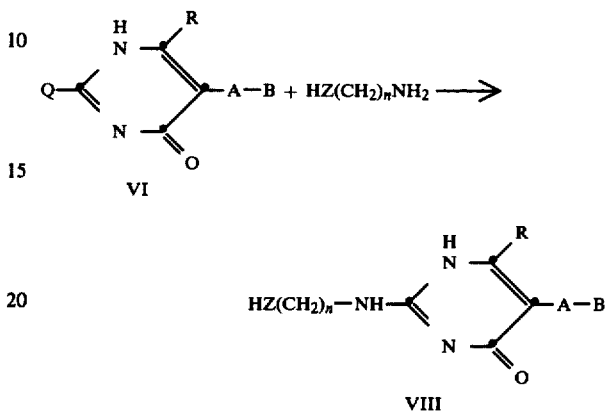

where R, A, B, n and Q have their previously assigned meanings and Z is O or S. The reaction is carried out in an inert solvent such as a lower alkanol.

The pyrimidone or pyrimidinethione moiety of the compounds of this invention (XX) is substituted in the 5 position with the grouping A-B where B may be an hydroxy substituted aryl or pyridyl radical. These hydroxy substituted radicals are conveniently prepared from the corresponding alkoxy substituted aryl or pyridyl group (B) by reaction with conc. aqueous HCl or 48% aqueous HBr in ethanol or other equivalent solvent at an elevated temperature. Alternatively, if it is desirable to use less stringent reaction conditions, BBr$_3$ can be used as the dealkylating agent in a suitable solvent, for example, methylene dichloride.

In the above reaction schemes, the aminoalkyl group present at position 2 of the thiazole ring has been shown as carrying through each of the reaction steps essentially unchanged from the starting material employed (I in Flow Chart A). In those instances where it is desired that either R$^1$ or R$^2$ or both be hydrogen in a final product (XX), alternate procedures must be used. For example, where R$^1$ is hydrogen but R$^2$ is alkyl, it is possible to carry a benzyl protecting group through a given reaction scheme to the preparation of the primary amine derivative (Va) at which point the benzyl group can be removed by catalytic hydrogenation to give a secondary amine grouping NHR$^2$. Similarly, an acyl protecting group can be used, such as a benzoyl group, and this protecting group is conveniently removed as by reduction to an alcohol during the lithium triethylborohydride reduction step by using excess borohydride. Similarly, if it is desired to have a primary aminoalkyl group at position 2 of the thiazole ring, a protecting group such as the phthalimido group can be utilized. In such instance, the starting material (I) would be one in which R$^1$ and R$^2$, when taken together with the nitrogen to which they are attached, form a phthalimido group. This grouping can be carried throughout the synthetic procedure until it is desired to remove it [after reaction of the ethylamine (V) with the pyrimidone (VI)] by hydrazinolysis or other hydrolytic procedure. Such a protecting group would be particularly valuable in those instances where it is desired to utilize a 4-chloromethylthiazole as an intermediate as in Flow Chart C. In the preferred synthetic procedure set forth in Flow Chart A, use of such protecting groups for a secondary aminoalkyl group at position 2 of the thiazole ring is not necessary.

An alternate procedure for preparing intermediates useful in the synthesis of compounds of this invention (XX) starts with the reaction of dichloroacetone and a substituted aminothioacetamide. The use of the resulting 4-chloromethylthiazole where not more than one of $R^1$ and $R^2$ is H has been discussed previously. However, this procedure is illustrated in Flow Chart F below and is particularly valuable in preparing the compounds of this invention wherein both $R^1$ and $R^2$ are H.

Flow Chart F

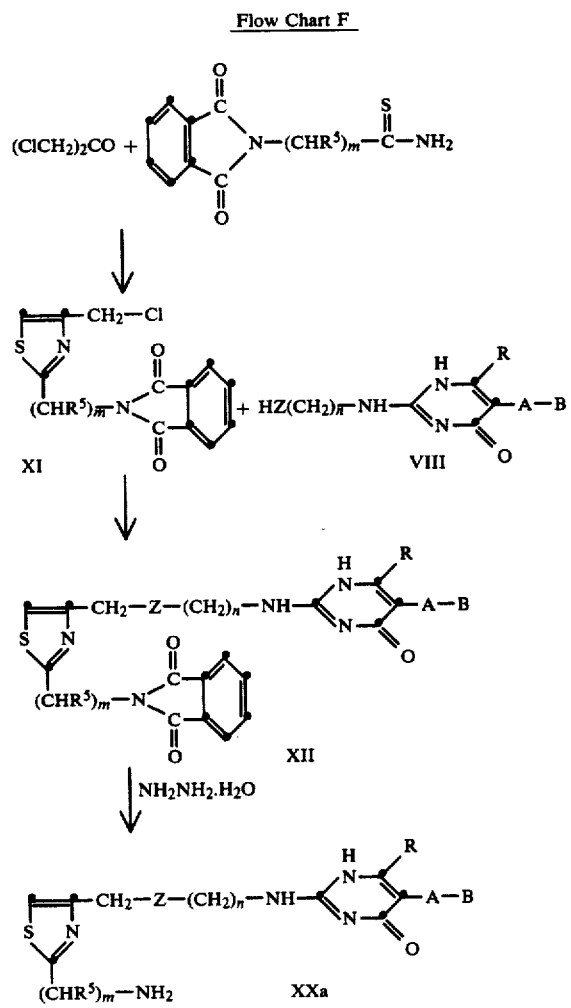

wherein R, $R^5$, A, m and n have their previously assigned significances.

In Flow Chart F, a 2-(phthalimidoalkylthioacetamide) reacts with dichloroacetone, following the procedure of J. Am. Chem. Soc., 64, 90 (1942), to yield a 2-(phthalimidoalkyl)-4-chloromethylthiazole. Reaction of this intermediate with a cysteamine (or homocysteamine) derivative in which the amine group is attached to a 4-pyrimidone of the desired structure provides a 2-(phthalimido)-4-thiazolyl derivative (XI) which group can be deprotected with hydrazine to yield the 2-aminoalkylthiazole derivative XXa in which $R^1$ and $R^2$ are H.

According to Flow Chart E the pyrimidone VI having a leaving group Q is reacted with cysteamine (or homocysteamine) of the corresponding hydroxy derivatives to yield a 2-(2-thio or oxy)ethylamino-5-substituted-4-pyrimidone (VIII). Reaction of this pyrimidone with a 2-aminoalkyl-4-thiazolylmethylchloride XI under reaction conditions sufficiently basic to produce an anion, illustratively a mercapto anion

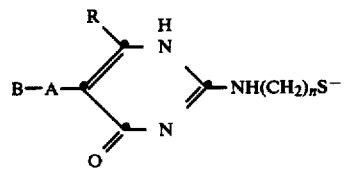

provides the compounds of this invention (XX) wherein Z is S or O (except that $R^1$ or $R^2$ may represent blocking groups).

Alternatively, the 2-(ω-mercaptoalkylamino)pyrimidone VIII as an acid addition salt can be fused with an acid addition salt of the 2-alkylamino-4-thiazolemethylchloride to yield the final product XX wherein X is O and Z is S.

The chloromethylthiazole VII where L is Cl is readily prepared by chlorination of the corresponding hydroxymethylthiazole (IV-Flow Chart A) with, for example, thionylchloride, $PCl_5$, $POCl_3$ etc. Alternatively, the procedure outlined in step one of Flow Chart F can be utilized, i.e., reaction of dichloroacetone with a phthalamidothioacetamide will yield directly a compound according to XI.

The primary thiazolylalkyl amine reactants Vc (V wherein Z is $CH_2$ and n is 1, 2 or 3) can be prepared by the procedure illustrated in Flow Chart G below.

Flow Chart G

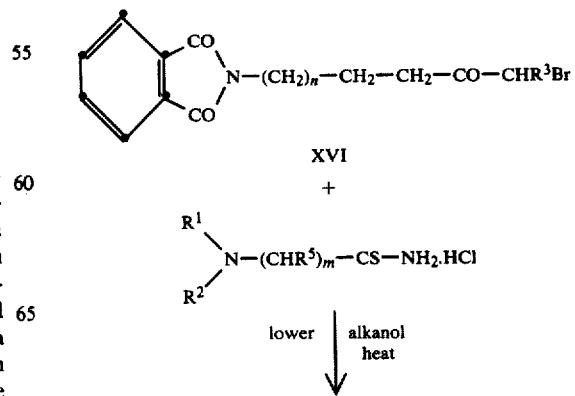

-continued
Flow Chart G

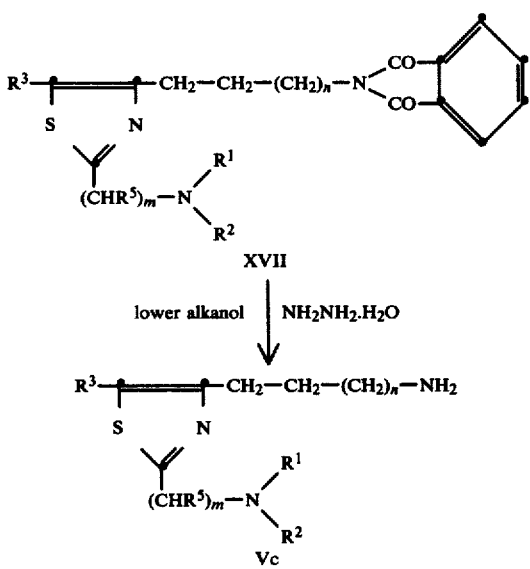

wherein $R^1$, $R^2$, $R^3$, $R^5$, n and m have their previously assigned meaning and at least one of $R^1$ and $R^2$ must be $C_1$-$C_3$)alkyl.

According to flow chart G, an omega (phthalimido)alkyl halomethyl ketone (XVI) is reacted with a dialkylaminothioacetamide hydrochloride to produce a 2-aminoalkyl-5-permissibly-substituted-4-(omega-phthalimido)alkylthiazole (XVII). The protecting group is removed by hydrolysis with hydrazine hydrate to produce the 4-(omega-aminoalkyl)thiazole ($V_c$). Alkaline hydrolysis with an alkali metal hydroxide followed by treatment with a dilute hydrochloric acid can also be used. This primary amine product (Vc) corresponds to the starting material ($V_a$) produced by flow chart A and can undergo each of the reactions set forth in Flow Charts B-D to produce the compounds of this invention wherein Z in formula XX is $CH_2$.

This invention is further illustrated by the following specific examples.

EXAMPLE 1

Preparation of 2-[2-(2-dimethylaminomethyl-4-thiazolylmethylthio)ethyl]amino-5-(3-pyridyl)methyl-4-pyrimidone.

A reaction mixture prepared from 1.24 g. of 2-nitroamino-5-(3-pyridyl)methyl-4-pyrimidone, 1.14 g. of 2-(2-dimethylaminomethyl-4-thiazolylmethylthio)ethylamine and 6 ml. of anhydrous ethanol was refluxed for about 1 day under a nitrogen atmosphere. The volatile constitutents were removed by evaporation to yield an oily residue. Water was added and the aqueous layer extracted with ether and with ethyl acetate. The organic extracts were combined, dried and evaporated to dryness to yield 2-[2-(2-dimethylaminomethyl-4-thiazolylmethylthio)ethyl]amino-5-(3-pyridyl)methyl-4-pyrimidone as a residue which was crystallized from ether. Recrystallization from an ethanol-ether solvent mixture yielded 2-[2-(2-dimethylaminomethyle-4-thiazolylmethylthio)ethyl]amino-5-(3-pyridyl)methyl-4-pyrimidone melting at 122°-123° C.; yield=0.68 g.

Analysis Calculated: C, 54.78; H, 5.81; N, 20.17: Found: C, 54.94; H, 5.65; N, 19.91.

EXAMPLE 2

Preparation of 2-[2-(2-dimethylaminomethyl-4-thiazolylmethylthio)ethyl]amino-5-[5-(1,3-benzodioxoly)]methyl-4-pyrimidone.

Following the procedure of Example 1, 1.09 g. of 2-(2-dimethylaminomethyl-4-thiazolymethylthio)ethylamine and 1.40 g. of 2-nitroamino-5-[5-(1,3-benzodioxolyl)]methyl-4-pyrimidone were dissolved in 6 ml. of anhydrous ethanol and the solution heated to reflux for about 1 day. The volatile constituents were removed by evaporation. The resulting residue was extracted with ethyl acetate and the ethyl acetate extract was washed with water, dried and the ethyl acetate removed therefrom by evaporation. Trituration with cyclohexane yielded crystalline material which was separated by filtration. Recrystallization for ethyl acetate yielded 0.38 g of 2-[2-(2-dimethylaminomethyl-4-thiazolylmethylthio)ethyl]amino-5-[5-(1,3-benzodioxoly)]methyl-4-pyrimidone melting at about 110°-111° C.

Analysis Calculated: C, 54.88; H, 5.48; N, 15.24: Found: C, 54.68; H, 5.22; N, 14.95.

EXAMPLE 3

Preparation of 2-[2-(2-dimethylaminomethyl-4-thiazolylmethylthio)ethyl]amino-5-(6-methyl-3-pyridyl)methyl-4-pyrimidone.

Following the procedure of Example 1, 0.75 g. of 2-(2-dimethylaminomethyl-4-thiazolylmethylthio)ethylamine and 0.78 g. of 2-nitroamino-5-(6-methyl-3-pyridyl)methyl-4-pyrimidone were dissolved in 5 ml. of anhydrous ethanol and the resulting solution refluxed for about 1 day. The solvents were removed by evaporation and the residue extracted with ethyl acetate. The ethyl acetate extract was washed with water and dried. Evaporation of the ethyl acetate yielded crystals of 2-[2-(2-dimethylaminomethyl-4-thiazolylmethylthio)ethyl]amino-5-(6-methyl-3-pyridyl)methyl-4-pyrimidone which melted at about 154°-5° C. after recrystallization from an ethyl acetate-ether solvent mixture; yield=0.56 g.

Analysis Calculated: C, 55.79; H, 6.09; N, 19.52: Found: C, 56.02; H, 6.06; N, 19.50.

EXAMPLE 4

Preparation of 2-[2-(2-dimethylaminomethyl-4-thiazolylmethylthio)ethyl]amino-5-(6-methoxy-3-pyridyl)methyl-4-pyrimidone.

Following the procedure of Example 1, 1.29 g. of 2-(2-dimethylaminomethyl-4-thiazolylmethylthio)ethylamine and 1.54 g. of 2-nitroamino-5-(6-methoxy-3-pyridylmethyl)-4-pyrimidone were dissolved in 50 ml. of ethanol and the resulting solution heated at reflux temperature for about 1 week. The solvent was removed by evaporation and the residue purified by gradient elution chromatography (silica-ethanol/ethyl acetate/ammonium hydroxide). Fractions containing the desired pyrimidone were combined and the solvents removed from the combined fractions. The resulting residue was crystallized from ethyl acetate to yield 2-[2-(2-dimethylaminomethyl-4-thiazolylmethylthio)ethyl]amino-5-(6-methoxy-3-pyridyl)methyl-4-pyrimidone melting at 137°-8° C.

Analysis Calculated: C, 53.79; H, 5.87; N, 18.82: Found: C, 53.53; H, 6.01; N, 18.72.

EXAMPLE 5

Preparation of 2-[2-(2-dimethylaminomethyl-4-thiazolylmethylthio)ethyl]amino-5-(5,6-dimethyl-3-pyridyl)methyl-4-pyrimidone.

Following the procedure of Example 1, 1.29 g. of 2-(2-dimethylaminomethyl-4-thiazolylmethylthio)ethylamine and 1.29 g. of 2-nitroamino-5-(5,6-dimethyl-3-pyridyl)methyl-4-pyrimidone were dissolved in 2.5 g. of anhydrous ethanol and the mixture heated to refluxing temperature for 51 hours. The solvent was removed by evaporation and the residue purified by high pressure liquid gradient elution chromatography (silica-ethanol/ethyl acetate/ammonium hydroxide). Fractions containing 2-[2-(2-dimethylaminomethyl-4-thiazolylmethylthio)amino-5-(5,6-dimethyl-3-pyridyl)methyl-4-pyrimidone were combined and the solvents removed from the combined fractions. An excess of ethanolic hydrogen chloride was added to the resulting residue. Evaporation of the ethanol yielded 2-[2-(2-dimethylaminomethyl-4-thiazolylmethylthio)ethyl]amino-5-(5,6-dimethyl-3-pyridyl)methyl-4-pyrimidone trihydrochloride melting at about 207°-210° C. after two-fold recrystallization from an ethanol/ethyl acetate solvent mixture; yield = 1.13 g.

Analysis Calculated: C, 45.54; H, 5.64; N, 5.17: Found: C, 45.29; H, 5.39; N, 5.21.

EXAMPLE 6

Preparation of 2-[2-(2-dimethylaminomethyl-4-thiazolylmethylthio)ethyl]amino-5-(6-hydroxy-3-pyridyl)methyl-4-pyrimidone.

A solution was prepared from 0.92 g. of 2-[2-(2-dimethylaminomethyl-4-thiazolylmethylthio)ethyl]amino-5-(6-methoxy-3-pyridyl)methyl-4-pyrimidone (from Example 4). A mixture of 25 ml. of ethanol and 25 ml. of 2N aqueous hydrochloric acid was added. The solution was heated to refluxing temperature for about 4 days after which time it was made basic by the addition of 5N aqueous sodium hydroxide. The volatile constituents were removed by evaporation. The resulting residue was triturated with ethanol and filtered. The solvent was removed from the filtrate and the residue chromatographed using high pressure liquid gradient elution chromatography (silica-ethanol/ethyl acetate/ammonium hydroxide). Fractions containing 2-[2-(2-dimethylaminomethyl-4-thiazolylmethylthio)ethyl]amino-5-(6-hydroxy-3-pyridyl)methyl-4-pyrimidone were combined and the solvent removed from the combined fractions. The residue was crystallized from a mixture of ethyl acetate and ether to yield 0.61 g. of 2-[2-(2-dimethylaminomethyl-4-thiazolylmethylthio)ethyl]amino-5-(6-hydroxy-3-pyridyl)methyl-4-pyrimidone melting at about 125°-128° C.

Analysis Calculated: C, 52.76; H, 5.59; N, 19.43: Found: C, 52.64; H, 5.39; N, 19.21.

EXAMPLE 7

Preparation of 2-[2-(2-dimethylaminomethyl-4-thiazolylmethylthio)ethyl]amino-5-(2-methoxy-4-pyridyl)methyl-4-pyrimidone.

Following the procedure of Example 1, a reaction mixture was prepared from 1.62 g. of 2-(2-dimethylaminomethyl-4-thiazolylmethylthio)ethylamine and 1.94 g. of 2-nitroamino-5-(2-methoxy-4-pyridyl)methyl-4-pyrimidone and 30 ml. of ethanol. The reaction mixture was stirred and heated at refluxing temperature for about 42 hours. The volatile constituents were removed by evaporation and the residue purified by high pressure liquid gradient elution chromatography (silica-ethanol/ethyl acetate/ammonium hydroxide). Fractions containing 2-[2-(2-dimethylaminomethyl-4-thiazolylmethylthio)ethyl]amino-5-(2-methoxy-4-pyridyl)methyl-4-pyrimidone were combined and the solvent removed therefrom. Recrystallization of the resulting residue from a cyclohexane-ether solvent mixture gave 2-[2-(2-dimethylaminomethyl-4-thiazolylmethylthio)ethyl]amino-5-(2-methoxy-4-pyridyl)methyl-4-pyrimidone melting at 79°-80° C.

Analysis Calculated: C, 53.79; H, 5.87; N, 18.82: Found: C, 53.53; H, 5.71; N, 18.64.

EXAMPLE 8

Preparation of 2-[2-(2-dimethylaminomethyl-4-thiazolylmethylthio)ethyl]amino-5-(3-pyridyl)methyl-6-methyl-4-pyrimidone.

A reaction mixture was prepared from 1.16 g. of 2-[2-dimethylaminomethyl-4-thiazolylmethylthio]ethylamine, 1.31 g. of 2-nitroamino-5-(3-pyridyl)methyl-6-methyl-4-pyrimidone and 25 ml. of anhydrous ethanol. The reaction mixture was heated at reflux temperature for about 5 days after which time the ethanol was removed by evaporation. The residue was chromatographed using high pressure liquid gradient elution chromatography (silica-ethanol/ethyl acetate/ammonium hydroxide). Fractions containing 2-[2-(2-dimethylaminomethyl-4-thiazolylmethylthio)ethyl]amino-5-(3-pyridyl)methyl-6-methyl-4-pyrimidone were combined and the solvents removed from the combined fractions. 1.1 g. of crystalline material was obtained which melted at about 130°-131° C. after recrystallization from a mixture of ethanol and ether; yield = 1.03 g. 2-[2-(2-dimethylaminomethyl-4-thiazolylmethylthio)ethyl]amino-5-(3-pyridyl)methyl-6-methyl-4-pyrimidone thus prepared had the following analysis:

Analysis Calculated: C, 55,79; H, 6.09; N, 19.52: Found: C, 55.73; H, 5.98; N, 19.31.

EXAMPLE 9

Preparation of 2-[2-(2-dimethylaminomethyl-4-thiazolylmethylthio)ethyl]amino-5-(2-hydroxy-4-pyridyl)methyl-4-pyrimidone.

Following the procedure of Example 6, a solution prepared from 0.51 g. of 2-[2-(2-dimethylaminomethyl-4-thiazolylmethylthio)ethyl]amino-5-(2-methoxy-4-pyridyl)methyl-4-pyrimidone (from Example 7) in 15 ml. of 2N aqueous hydrochloric acid and 10 ml. of ethanol was heated to refluxing temperature for about 5 days. Volatile constituents were then removed by evaporation and the resulting residue was dissolved in water. The acidic aqueous solution was neutralized with ammonium hydroxide. Water was removed by evaporation. The residue was extracted several times with ethanol. The ethanol was removed from the combined ethanol extracts by evaporation. The residue remaining was purified by high pressure liquid gradient elution chromatography (silica-ethanol/ethyl acetate/ammonium hydroxide). Fractions containing 2-[2-(2-dimethylaminomethyl-4-thiazolylmethylthio)ethyl]amino-5-(2-hydroxy-4-pyridyl)methyl-4-pyrimidone were combined and the solvent removed therefrom by evaporation. Crystallization of the residue from ethyl acetate yielded 200 mg. of 2-[2-(2-dimethylaminomethyl-4-thiazolylmethylthio)ethyl]amino-5-(2-hydroxy-4-pyridyl)methyl-4-pyrimidone melting at 152°-154° C. having the following analysis.

Analysis Calculated: C, 52.76; H, 5.59; N, 19.43: Found: C, 52.50; H, 5.49; N, 19.22.

EXAMPLE 10

Preparation of 2-[2-(2-dimethylaminomethyl-4-thiazolylmethylthio)ethyl]amino-5-(2-pyridyl)methyl-4-pyrimidone.

Following the procedure of Example 1, a reaction mixture was prepared from 1.62 g. of 2-(2-dimethylaminomethyl-4-thiazolylmethylthio)ethylamine, 1.73 g. of 2-nitroamino-5-(2-pyridyl)methyl-4-pyrimidone and 20 ml. of ethanol. The reaction mixture was heated at refluxing temperature for about 21 hours. The solvents were removed in vacuo and the residue purified by high pressure liquid gradient elution chromatography (silica-ethanol/ethyl acetate/ammonium hydroxide). Fractions containing 2-[2-(2-dimethylaminomethyl-4-thiazolylmethylthio)ethyl-amino-5-(2-pyridyl)-methyl-4-pyrimidone (as determined by TLC) were combined and the solvents removed from the combined fractions by evaporation. The resulting crystalline residue was dissolved in ethanol and a slight excess of 5N aqueous hydrochloric acid added. The reaction mixture was evaporated to dryness and the resulting crystalline residue recrystallized from a mixture of methanol and ethanol to yield 1.2 g. of 2-[2-(2-dimethylaminomethyl-4-thiazolylmethylthio)ethyl]amino-5-(2-pyridyl)methyl-4-pyrimidone trihydrochloride melting at 205°–207° C.

Analysis Calculated: C, 43.39; H, 5.17; N, 15.98: Found: C, 43.11; H, 5.21; N, 16.01.

EXAMPLE 11

Preparation of 2-[2-(2-dimethylaminomethyl-4-thiazolylmethylthio)ethyl]amino-5-(4-pyridyl)methyl-4-pyrimidone.

Following the procedure of Example 1, 2-nitroamino-5-(4-pyridyl)methyl-4-pyrimidone was reacted with 2-(2-dimethylaminomethyl-4-thiazolylmethylthio)ethylamine to yield 2-[2-(2-dimethylaminomethyl-4-thiazolylmethylthio)ethyl]amino-5-(4-pyridyl)methyl-4-pyrimidone as a trihydrochloride salt melting at 200°–202° C. after recrystallization from a methanol/ethanol solvent mixture.

Analysis Calculated: C, 43.39; H, 5.17; N, 15.98: Found: C, 43.37; H, 5.33; N, 15.71.

EXAMPLE 12

Preparation of 2-[2-(2-dimethylaminomethyl-4-thiazolylmethylthio)ethyl]amino-5-(3-pyridyl)methoxy-4-pyrimidone A reaction mixture was prepared from 1.26 g. of 2-(2-dimethylaminomethyl-4-thiazolylmethylthio)ethylamine and 1.36 g. of 2-methylthio-5-(3-pyridyl)methoxy-4-pyrimidone in 20 ml. of pyridine. The reaction mixture was heated to reflux temperature for about 2 days. The pyridine was then removed by evaporation in vacuo and the resulting residue subjected to high pressure liquid chromatography over silica. Fractions shown by tlc to contain the desired compound were combined and the combined fractions rechromatographed on a silica preparative plate using 3% ammoniated ethanol as the solvent. 2-[2-(2-Dimethylaminomethyl-4-thiazolylmethylthio)ethyl]amino-5-(3-pyridyl)methoxy-4-pyrimidone free base thus obtained was converted to the trihydrochloride salt by standard procedures. Recrystallization of the crude trihydrochloride salt from ethanol yielded 2-[2-(2-dimethylaminomethyl-4-thiazolylmethylthio)ethyl]amino-5-(3-pyridyl)methoxy-4-pyrimidone trihydrochloride melting at 183°–185° C.

Analysis Calculated: C, 42.11; H, 5.02; N, 15.51: Found: C, 42.35; H, 5.11; N, 15.71.

EXAMPLE 13

Preparation of 2-[2-(2-dimethylaminomethyl-4-thiazolylmethylthio)ethyl]amino-5-(3-pyridyl)methyl-4-pyrimidinethione Following the procedure of Example 12, a mixture of 1.11 g. of 2-(2-dimethylaminomethyl-4-thiazolylmethylthio)ethylamine and 1.24 g. of 2-methylthio-5-(3-pyridyl)methyl-4-pyrimidinethione in 15 ml. of pyridine was refluxed for 2 days. The desired reaction product was purified by gradient elution high pressure liquid chromatography over silica using an ethyl acetate/ethanol/ammonium hydroxide solvent system as the eluant. Fractions shown by tlc to contain 2-[2-(2-dimethylaminomethyl-4-thiazolylmethylthio)ethyl]amino-5-(3-pyridyl)methyl-4-pyrimidinethione free base were combined and the solvent removed by evaporation.

The free base was converted to the corresponding trihydrochloride salt by standard procedures. Recrystallization of the trihydrochloride salt from ethanol yielded 2-[2-(2-dimethylaminomethyl-4-thiazolylmethylthio)ethyl]amino-5-(3-pyridyl)methyl-4-pyrimidinethione trihydrochloride (0.8 g) melting at 187°–189° C.

Analysis Calculated: C, 42.10; H, 5.02; N, 15.51: Found: C, 42.06; H, 4.83; N, 15.75.

EXAMPLE 14

Preparation of 2-[2-(2-Dimethylaminomethyl-4-thiazolylmethylthio)ethyl]amino-5-(6-methyl-3-pyridyl)oxy-4-pyrimidone.

Following the procedure of Example 12, a mixture of 1.29 g. of 2-(2-dimethylaminomethyl-4-thiazolylmethylthio)ethylamine and 1.38 g. of 2-methylthio-5-(6-methyl-3-pyridyl)oxy-4-pyrimidone in pyridine solution were heated to refluxing temperature for about 88 hours. After this time, the solvent was removed by evaporation in vacuo and the residue dissolved in ethanol. The ethanolic solution was evaporated to dryness. The residue was subjected to high pressure liquid chromatography over silica using a gradient elution technique with an ethyl acetate/ethanol/ammonium hydroxide solvent system as the eluant. Fractions shown by tlc to contain 2-[2-(2-dimethylaminomethyl-4-thiazolylmethylthio)ethyl]amino-5-(6-methyl-3-pyridyl)oxy-4-pyrimidone were combined and the solvent removed by evaporation. The resulting residue was rechromatographed on a silica preparative plate using 3% ammoniated ethanol as the solvent. 2-[2-(2-Dimethylaminomethyl-4-thiazolylmethylthio)ethyl]amino-5-(6-methyl-3-pyridyl)oxy-4-pyrimidone free base thus obtained was converted to the corresponding trihydrochloride salt by standard procedures. 2-[2-(2-Dimethylaminomethyl-4-thiazolylmethylthio)ethyl]amino-5-(6-methyl-3-pyridyl)oxy-4-pyrimidone trihydrochloride melted at about 216°–220° C. after recrystallization from a mixture of ethanol, ethyl acetate and ether. Yield = 0.36 g.

Analysis Calculated: C, 42.11; H, 5.02; N, 15.51: Found: C, 42.34; H, 5.21; N, 15.39.

EXAMPLE 15

Preparation of 2-[2-(2-dimethylaminomethyl-4-thiazolylmethylthio)ethyl]amino-5-[2-(3-pyridyl)ethyl]-4-pyrimidone.

Following the procedure of Example 12, a mixture of 1.29 g. of 2-(2-dimethylaminomethyl-4-thiazolylmethylthio)ethylamine and 1.37 g. of 2-methylthio-5-[2-(3-pyridyl)ethyl]-4-pyrimidone in 25 ml. of anhydrous pyridine was heated to refluxing temperature for about 4 days. The solvent was removed in vacuo. The residue was dissolved in ethanol and the ethanol evaporated. The residue was purified by high pressure liquid chromatography over silica using a gradient elution technique with an ethyl acetate/ethanol/ammonium hydroxide solvent system as the eluant. Fractions shown by tlc to contain the desired product were combined and the combined fractions rechromatographed on a silica preparative plate using 3% ammoniated ethanol as the solvent. 2-[2-(2-Dimethylaminomethyl-4-thiazolylmethylthio)ethyl]amino-5-[2-(3-pyridyl)ethyl]-4-pyrimidone free base thus prepared was converted by standard procedures to the trihydrochloride salt which melted at 226°–228° C. after recrystallization from an ethanol/ethyl acetate/ether solvent mixture. Yield=1.0 g.

Analysis Calculated: C, 44.49; H, 5.41; N, 15.56: Found: C, 44.24; H, 5.29; N, 15.34.

The following additional compounds were prepared by the above procedure:

2-[2-(2-N-Pyrrolidinomethyl-4-thiazolylmethylthio)ethyl]amino-5-(6-methyl-3-pyridyl)methyl-4-pyrimidone from 2-(2-N-pyrrolidinomethyl-4-thiazolylmethylthio)ethylamine and 2-methylthio-5-[2-(6-methyl-3-pyridyl)methyl]-4-pyrimidone. Yield=38% m.p. 159°–160.5° C.

Molecular ion (free base) at 456

Analysis Calculated: C, 57.87; H, 6.18; N, 18.40; Found: C, 57.65; H, 6.09; N, 18.17.

2-[2-(2-Dimethylaminomethyl-4-thiazolylmethylthio)ethyl]amino-5-(2-methyl-4-pyridyl)methyl-4-pyrimidone, trihydrochloride from 2-(2-dimethylaminomethyl-4-thiazolylmethylthio)ethylamine and 2-methylthio-5-(2-methyl-4-pyridyl)methyl-4-pyrimidone. Yield=18% m.p. 191°–193° C.

Molecular ion (free base) at 430

Analysis Calculated: C, 44.49; H, 5.41; N, 15.56; Found: C, 44.31; H, 5.39; N, 15.35.

2-[2-(2-Dimethylaminomethyl-4-thiazolylmethylthio)ethyl]amino-5-(2-thiazolyl)methyl-4-pyrimidone from 2-(2-dimethylaminomethyl-4-thiazolylmethylthio)ethylamine and 2-nitroamino-5-(2-thiazolyl)methyl-4-pyrimidone. Yield=53% m.p. 115°–116° C.

Molecular ion at 422

Analysis Calculated: C, 48.32; H, 5.25; N, 19.89; Found: C, 48.27; H, 5.52; N, 20.18.

2-[2-(2-Dimethylaminomethyl-4-thiazolylmethylthio)ethyl]amino-5-(2-furyl)methyl-4-pyrimidone, dihydrochloride from 2-(2-dimethylaminomethyl-4-thiazolylmethylthio)ethylamine and 2-nitroamino-5-(2-furyl)methyl-4-pyrimidone. Yield=33% m.p. 156°–158° C.

Molecular ion (free base) 405

Analysis Calculated: C, 45.19; H, 5.27; N, 14.64; Found: C, 45.18; H, 5.22; N, 14.48.

2-[2-(2-Methylaminomethyl-4-thiazolylmethylthio)ethyl]amino-5-(6-methyl-3-pyridyl)methyl-4-pyrimidone from 2-(2-methylaminomethyl-4-thiazolylmethylthio)ethylamine and 2-methylthio-5-(6-methyl-3-pyridyl)methyl-4-pyrimidone. Yield=15% m.p. 192°–194° C.

Molecular ion (free base) at 416

Analysis Calculated: C, 43.39; H, 5.17; N, 15.98; Found: C, 43.65; H, 5.32; N, 15.86.

2-[2-(2-Dimethylaminomethyl-4-thiazolylmethylthio)ethyl]amino-5-(5-methyl-3-pyridyl)methyl-3-pyridyl)methyl-4-pyrimidone, trihydrochloride hydrate (3.5 H$_2$O) from 2-(2-dimethylaminomethyl-4-thiazolylmethylthio)ethylamine and 2-methylthio-5-(5-methyl-3-pyridyl)methyl-4-pyrimidone. Yield=6% m.p. 80° C. (foam), 220°–240° C. (dec.).

Molecular ion at 431

2-[2-(2-Dimethylaminomethyl-4-thiazolylmethylthio)ethyl]amino-5-(2-methoxy-3-pyridyl)methyl-4-pyrimidone from 2-(2-dimethylaminomethyl-4-thiazolylmethylthio)ethylamine and 2-nitroamino-5-(2-methoxy-3-pyridyl)methyl-4-pyrimidone. Yield=44%

Molecular ion at 447

Analysis Calculated: C, 53.79; H, 5.87; N, 18.82; Found: C, 53.55; H, 6.03; N, 18.59.

2-[2-(2-Dimethylaminomethyl-4-thiazolylmethylthio)ethyl]amino-5-(2-hydroxy-3-pyridyl)methyl]-4-pyrimidone, dihydrochloride was prepared by reacting 2-(2-dimethylaminomethyl-4-thiazolylmethylthio)ethylamine with 2-nitroamino-5-(2-methoxy-3-pyridyl)methyl-4-pyrimidone, followed by hydrolysis of the 2-methoxy substituent in the initial product with hydrochloric acid to yield a 2-hydroxy group. Yield=11% m.p. 118°–123° C. (after recrystallization from EtOAc-Et$_2$O) 2-[2-(2-Dimethylaminomethyl-4-thiazolylmethylthio)ethyl]amino-5-(2-tetrahydrofuryl)methyl-4-pyrimidone, dihydrochloride from 2-(2-dimethylaminomethyl-4-thiazolylmethylthio)ethylamine and 2-nitroamino-5-(2-tetrahydrofuryl)methyl-4-pyrimidone. Yield=39% m.p. 178°–180° C.

EXAMPLE 16

2-[2-(2-Dimethylaminomethyl-4-thiazolylmethylthio)ethyl]amino-5-(imidazol-4-yl)methyl-4-pyrimidone.

A solution of 2-(dimethylaminomethyl-4-thiazolylmethylthio)ethylamine (2.3 g) and 2-nitroamino-5-[1-(4,4'-dimethoxybenzhydryl)imidazol-4-ylmethyl]-4-pyrimidone (4.62 g) in ethanol (11 ml) was refluxed for 22 hours. Ethanol was evaporated from the solution and the residue chromatographed using HPLC. The appropriate fractions were combined and freed of solvents to give about 1.6 g of 2-[2-(2-dimethylaminomethyl-4-thiazolylmethylthio)ethyl]amino-5-[1-(4,4'-dimethoxybenzhydryl)imidazol-4-ylmethyl]-4-pyrimidone as a glass.

A solution consisting of about 1.6 g of the compound prepared above, 3 ml of anisole and 30 ml of trifluoroacetic acid was refluxed for 3 hours, at which time no starting material remained, as determined by TLC. Volatile components were evaporated from the solution and 5N HCL and ethanol were added to the residue. The solution was again evaporated to dryness. Water was added to the residue and the solution was extracted with ether. The acid aqueous solution was made basic with potassium carbonate and the basic solution evaporated to dryness. Isopropanol was added to the residue and evaporated. The resulting residue was extracted with several aliquots of hot isopropanol. The combined extracts, after cooling, were filtered to remove inorganic salts. The solvent was evaporated from the filtrate to give a glass consisting of the title product. The crude product was purified by HPLC and was obtained as an amorphous solid. m/e 406,P+1.

Preparation 1

Preparation of Ethyl 2-Dimethylaminomethyl-4-thiazolecarboxylate

A reaction mixture was prepared containing 15.5 g. of dimethylaminothioacetamide hydrochloride, 20.5 g. of ethyl bromopyruvate and 100 ml. of ethanol. The reaction mixture was heated to refluxing temperature for about four hours after which time the solvent was removed in vacuo in a rotary evaporator. The residue, containing ethyl 2-dimethylaminomethyl-4-thiazolecarboxylate formed in the above reaction, was dissolved in a mixture of ether and water. The aqueous layer was separated. The ether layer was extracted with an equal volume of water and then discarded. The two aqueous layers were combined and washed with ether. The ether layer was again discarded and the aqueous layer cooled to a temperature in the range of 0°-5° C. Solid potassium carbonate was added until the aqueous layer gave a basic reaction to litmus. An oil separated comprising ethyl 2-dimethylaminomethyl-4-thiazolecarboxylate free base. The oily layer was extracted with ether and the ether extract separated and dried. The ether was removed by evaporation in vacuo. The resulting residue was purified by gradient high pressure liquid chromatography (silica ethyl acetate). Ethyl 2-dimethylaminomethyl-4-thiazolecarboxylate thus obtained had the following physical characteristics:

Analysis Calculated: C, 50.45; H, 6.59; N, 13.07; S, 14.96; Found: C, 50.13; H, 6.39; N, 12,89; S, 15.04.

The nmr spectrum in CDCl$_3$ (TMS internal standard) gave the following signals ($\delta$): 1.43 (triplet, 3H), 2.40 (singlet, 6H), 3.87 (singlet, 2H) 4.47 (quartet, 2H), 8.29 (singlet, 1H).

Following the above procedure, a solution containing 20.4 g. of ethyl bromopyruvate and 20.8 g. of N-methyl-N-benzoyl thioacetamide in 100 ml. of ethanol was heated to refluxing temperature for about 4 hours. The solvent was removed by evaporation in vacuo and the resulting residue dissolved in 65 ml. of 4.5N aqueous hydrochloric acid. The aqueous acidic layer was extracted with ether and the ether extract discarded. 11.5 g. of sodium carbonate were added to the aqueous layer. Ethyl 2-(methylbenzoylaminomethyl)-4-thiazolecarboxylate formed in the above reaction, being insoluble in the solution, separated and was extracted into ether. The ether extract was separated and dried. Evaporation of the ether yielded 20.2 g. of ethyl 2-(methylbenzoylaminomethyl)-4-thiazolecarboxylate melting at about 151.5°-153.5° C. after recrystallization from ethyl acetate.

Analysis Calculated: C, 59.19; H, 5.30; N, 9.20; Found: C, 58.98; H, 5.25; N, 8.90.

The nmr spectrum in CDCl$_3$ (TMS internal standard) gave the following signals ($\delta$): 1.42 (triplet, 3H), 3.07 (singlet, 3H), 4.41 (quartet, 2H), 4.98 (singlet, 2H), 7.40 (apparent singlet, 5H), 8.16 singlet, 1H).

Preparation 2

Preparation of 2-Dimethylaminomethyl-4-thiazolemethanol

A solution of 12.5 g. of ethyl 2-dimethylaminomethyl-4-thiazolecarboxylate dissolved in about 35 ml. of anhydrous tetrahydrofuran was prepared and then cooled to about 0° C. under a nitrogen atmosphere. About 130 ml. of a 1 molar solution of lithium triethylborohydride in THF was added in dropwise fashion while maintaining the temperature in the range 0°-5° C. The reaction mixture was stirred for about two hours after which time 36 ml. of 6N aqueous hydrochloric acid were added while maintaining the temperature in the range −3° C. to 0° C. The volatile constituents were removed in vacuo on a rotary evaporator. Water was added to the resulting residue and again the volatile constituents were removed. Water was again added to the residue and the aqueous mixture extracted several times with ether. The ether extracts were separated and discarded. The aqueous solution was then chilled and made basic by the addition of solid potassium carbonate. The resulting alkaline aqueous mixture was extracted with ethyl acetate. 2-Dimethylaminomethyl-4-thiazolemethanol, being insoluble in the basic solution, separated and was extracted with several portions of ethyl acetate. The ethyl acetate extracts were combined, and the combined extracts washed with saturated aqueous sodium chloride and then dried. The ethyl acetate was removed by evaporation. The residue consisting of a brown oil weighing about 7.7 g. comprised 2-dimethylaminomethyl-4-thiazolemethanol formed in the above reaction having the following physical characteristics.

Analysic Calculated: C, 48.81; H, 7.02; N, 15.26; Found: C, 48.71; H, 6.77; N, 15.85.

The nmr spectrum in CDCl$_3$ (TMS internal standard) gave the following signals ($\delta$): 2.33 (singlet, 6H), 3.74 (singlet, 2H), 4.32 (singlet, 1H), 4.72 (singlet, 2H), 7.15 (singlet, 1H)

Boiling point = 102° C. at 0.5 torr.

Following the above procedure, 22.5 g. of ethyl N-methyl-N-benzoyl 2-aminomethyl-4-thiazolecarboxylate were dissolved in 125 ml. of dry THF under a nitrogen atmosphere. 320 ml. of a 1M LiEt$_3$BH in THF was added. (Excess borohydride was required over the amount in the above example because of the necessity of reducing both the ethyl ester group to a hydroxymethyl group and of removing the benzoyl group as benzyl alcohol leaving a secondary amine). The reaction mixture was worked up in accordance with the above procedure by decomposition with 6N aqueous hydrochloric acid and water. The residue remaining after the volatile constituents had been removed was a thick oil which was taken up in a little water and 60 ml. of ether. 1 ml. of 12N aqueous hydrochloric acid was added, thus making the aqueous phase strongly acidic. The ether layer was separated and the aqueous layer extracted five more times with equal portions of ether. The ether extracts were discarded. The water layer was separated and the water removed by evaporation in vacuo. The acidic residue was made strongly basic (while being cooled) with 50% aqueous sodium hydroxide (6 grams in 6 ml. of water). 2-Methylaminomethyl-4-thiazolemethanol produced by the above series of reactions was insoluble in the alkaline layer and separated. The compound was taken up in ethyl acetate using a continuous extractor. Removal of the solvent left a tannish oil residue weighing 10.7 grams comprising 2-methylaminomethyl-4-thiazolemethanol. The compound was converted to the dihydrochloride salt by standard laboratory procedures.

Alternatively, a mixture of 2.14 g of ethyl 2-dimethylaminomethyl-4-thiazolecarboxylate and 0.38 g of sodium borohydride in 20 ml. of isopropanol was heated with stirring at reflux temperature for about 14 hours. The reaction mixture was cooled, and 2 ml. of water were added carefully followed by 4 ml. of 5N aqueous hydrochloric acid. The volatile constituents were removed by evaporation. Methanol (10 ml.) was added and the mixture heated to refluxing temperature for about one hour. Methanol was removed by evaporation and the residual solids digested in 10 ml. of isopropanol on the steam bath. The isopropanol solution was separated by decantation and the solids reextracted with 10 m. of isopropanol. The isopropanol solutions and extracts were combined and the combined solution filtered while hot to remove insoluble material. The filtrate was chilled and a crystalline solid appeared which separated and was recovered by filtration. Recrystallization of the filter cake from isopropanol gave 1.73 g of 2-dimethylaminomethyl-4-thiazolemethanol hydrochloride melting at 153°–154° C.

Analysis: calculated: C, 40.28; H, 6.28; Cl, 16.99; N, 13.42. Found: C, 40.38; H, 5.04; Cl, 17.24; N, 13.12.

The methanols produced by the process of this example are readily converted to the corresponding thiazole-methyl chlorides according to the following procedure: A suspension was prepared from 1.05 grams of 2-dimethylaminomethyl-4-thiazolemethanol hydrochloride and 15 ml. of chloroform. Thionyl chloride (2.50 g) was added and the resulting mixture was stirred at reflux temperature for about 2.75 hours. Any volatile constituents including excess thionyl chloride were removed by evaporation. The residue was suspended in chloroform and the chloroform removed by evaporation. The residue was then recrystallized from a methanol-ethyl acetate solvent mixture to yield 2-dimethylaminomethyl-4-thiazolylmethchloride hydrochloride melting at 136°–8° C.

Analysis: calculated: C, 37.01; H, 5.32; Cl, 31.21; N, 12.33. Found: C, 37.13; H, 5.06; Cl, 31.41; N, 12.36.

Preparation 3

Preparation of 2-(2-Dimethylaminomethyl-4-thiazolylmethylthio)ethylamine

A reaction mixture was prepared from 18.8 g. of 2-dimethylaminomethyl-4-thiazolemethanol, 12.8 g. of 2-aminoethanethiol hydrochloride (cysteamine hydrochloride) and 160 ml. of 48% aqueous hydrobromic acid. The reaction mixture was stirred at about 100° C. for about 11 hours. The volatile constituents were removed in vacuo on a rotary evaporator. Water was added and the volatile constituents again removed by evaporation. The resulting residue, comprising 2-(2-dimethylaminomethyl-4-thiazolylmethylthio)ethylamine trihydrobromide formed in the above reaction, was dissolved in ethanol. The ethanol was evaporated and the resulting residue again dissolved in ethanol. Evaporation of the ethanol yielded a hygroscopic residue which was recrystallized from a methanol-ethyl acetate solvent mixture. 2-(2-Dimethylaminomethyl-4-thiazolylmethylthio)ethylamine trihydrobromide thus prepared had the following physical characteristics:

Analysis calculated: C, 22.80; H, 4.25; Br, 50.56; N, 8.86; S, 13.53. Found: C, 23.02; H, 4.31; Br, 50.64; N, 8.80; S, 13.60.

The nmr spectrum in DMSOd$_6$ (TMS internal standard) gave the following signals ($\delta$): 2.55–3.2 (multiplet, 4H), 2.84 (singlet 6H), 3.92 (singlet, 2H), 4.74 (singlet, 2H), 7.2–7.7 (broad, 1H), 7.94 (singlet, 1H), 7.92 (broad, 3H), 10.22 (broad, 1H).

Following the above procedure, 10.1 millimoles of 2-(methylaminomethyl)-4-thiazolemethanol dihydrochloride, 1.15 g. of cysteamine hydrochloride and 15 ml. of 48% aqueous hydrobromic acid were stirred at about 100° C. for about 7.5 hours. Water and hydrobromic acid were removed on a rotary evaporator and the resulting residue comprising 2-(2-methylaminomethyl-4-thiazolylmethylthio)ethylamine trihydrobromide formed in the above reaction was dissolved in water and the water removed by evaporation. The residue was again taken up in water and the water removed by evaporation. The residue was then dissolved in a small volume of water and a solution of 5.5 g. of potassium carbonate in 15 ml. of water was added. The resulting alkaline solution was evaporated to dryness. The resulting residue, comprising the free base of 2-(2-methylaminomethyl-4-thiazolylmethylthio)ethylamine, was slurried with ethanol and the ethanol separated and removed by evaporation. The residue was twice slurried with isopropanol. The residue was next extracted with boiling isopropanol several times and the combined isopropanol extracts combined and filtered. Removal of the isopropanol yielded a yellow oil. The yellow oil was dissolved in chloroform and the chloroform solution filtered. Chloroform was evaporated from the filtrate to yield 1.59 g. of a yellow oil comprising 2-(2methylaminomethyl-4-thiazolylmethylthio)ethylamine. The compound had the following physical characteristics:

The nmr spectrum is CDCl$_3$ (TMS internal standard) gave the following signals ($\delta$): 1.53 (overlapping singlets, 3H), 2.53 (singlet 3H), 2.62 (triplet, 2H), 2.86 (triplet, 2H), 3.81 (singlet, 2H), 4.04 (singlet, 2H), 7.04 (singlet, 1H).

The above primary amine can be prepared by an alternate procedure involving the fusion of a 2-dialkylaminoalkyl-4-isothiazolylmethylchloride acid addition salt with an acid addition salt of cysteamine (or homocysteamine). This alternate procedure is illustrated below.

2-Dimethylaminomethyl-4-thiazolylmethylchloride hydrochloride (1.92 g.) and cysteamine hydrochloride (0.96 g.) were intimately mixed and the mixture heated slowly under anhydrous conditions to about 100° C. over a period of one hour. The reaction mixture was then heated in the range 104°–110° C. for a period of 6 hours at which time the reaction was substantially complete as determined by tlc [silica-95:5 ethanol-NH$_4$OH (0.88 sp. gr.)]. The reaction mixture was cooled and the cooled melt dissolved in a minimal amount of water. The solution was transferred to a rotary evaporator and the water removed. The resulting residue solidified and the solid was recrystallized from a methanol-ethyl acetate solvent mixture. Hygroscopic crystals of 2-(2-dimethylaminomethyl-4-thiazolylmethylthio)ethyl amine trihydrochloride thus produced melted at about 165°–72° C. with evolution of HCl.

Analysis calculated: C, 31.72; H, 5.91; Cl, 31.21; N, 12.33; S, 18.82. found: C, 31.63; H, 6.15; Cl, 31.34; N, 12.62; S, 18.63.

Preparation 4

Preparation of 2-[2-(3-dimethylamino)propyl4-thiazolylmeththio]ethylamine

A reaction mixture was prepared containing 95.2 g. of 4-dimethylaminobutyronitrile, 134.3 g. of pyridine, 257.6 g. of triethylamine and 113 g. of H$_2$S. The reaction mixture was placed in an autoclave and the autoclave shaken for about 16 hours at 55° C. The reaction mixture was then removed from the autoclave and the volatile constituents removed by evaporation in vacuo.

The resulting residue comprising 4-dimethylaminothiobutyramide formed in the above reaction was digested with about 1.5 l. of boiling ethyl acetate. The mixture thus produced was filtered through cellulose (hyflo supercel). The filtrate was concentrated until crystals appeared. The crystals were separated by filtration and the separated crystals washed with ethyl acetate. Sixty grams of 4-dimethylaminothiobutyramide melting at about 77° C. were obtained.

Analysis: calculated: C, 49.27; H, 9.65; N, 19.15; found: C, 49.07; H, 9.59; N, 18.99.

A suspension was prepared from 14.6 g. of 4-dimethylaminothiobutyramide in 50 ml. of ethanol. The suspension was chilled. A cold solution of 3.65 g. of anhydrous hydrogen chloride in 50 ml. of anhydrous ethanol was added followed by 21.5 g. of ethyl bromopyruvate. The resulting reaction mixture was stirred at ambient temperature for about one hour and then was heated to refluxing temperature for an additional 2.25 hours. The volatile constituents were removed by evaporation in vacuo and the resulting residue taken up in a mixture of water and diethyl ether. The aqueous layer was separated and the separated layer extracted with several equal portions of ether. The aqueous solution was again chilled and then made basic (pH=10) by the addition of solid sodium bicarbonate and sodium carbonate. Ethyl 2-(3-dimethylamino)propyl-4-thiazolecarboxylate, being insoluble in the alkaline aqueous solution, separated and was extracted into ether. The ether extracts were combined and dried and the ether removed therefrom by evaporation in vacuo yielding 21 g. of the carboxylate ester as an oil. The compound had the following physical characteristics.

Thin layer chromatography (silica-95:5 ethanol/ammonia solvent system): $R_f$=0.43.

nmr (CDCl$_3$-TMS)$\delta$: 1.46 (triplet, 3H); 2.27 (singlet, 6H); 1.8–2.6 (multiplets, approx. 4H); 3.24 (triplet, 2H); 4.43 (quartet, 2H); 8.04 (singlet, 1H).

Following the procedure of Example 2, ethyl 2-(3-dimethylamino)propyl-4-thiazolecarboxylate was reduced with lithium triethylborohydride to yield 2-(3-dimethylamino)propyl-4-thiazolemethanol as an oil. The compound had the following physical characteristics.

Thin layer chromatography, $R_f$=0.42 (silica-95.5 ethanol/ammonium hydroxide solvent system).

nmr (CDCl$_3$-TMS)$\delta$: 2.15 (singlet, 6H); 1.62–2.50 (multiplets, approx. 4H); 2.05 (triplet, 2H); 3.75 (very broad, approx. 1H); 4.65 (singlet, 2H); 7.0 (singlet, 1H).

About 2.0 g of the above 4-thiazolemethanol were dissolved in ethanol to which was added 0.36 g. of anhydrous hydrogen chloride in ethanol. The ethanol was removed by evaporation and the resulting residue triturated with ethyl acetate. Crystallization occurred and the crystals were separated by filtration. Recrystallization from a mixture of methanol and ethyl acetate gave 2-(3-dimethylamino)propyl-4-thiazolemethanol hydrochloride melting at 125°–127° C.

Analysis: calculated: C, 45.66; H, 7.24; N, 11.83; found: C, 45.38; H, 7.39; N, 11.63.

A reaction mixture was prepared from 1.43 g. of the above thiazolemethanol hydrochloride, an equal weight of thionyl chloride and 35 ml. of chloroform. The reaction mixture was heated to refluxing temperature with stirring for about 3.5 hours. The volatile constituents were removed in vacuo and the crystalline residue was triturated with ethyl acetate. The ethyl acetate suspension was filtered. Recrystallization of the filter cake from a mixture of methanol and ethyl acetate yielded 4-(chloromethyl)-N,N-dimethyl-2-thiazolepropanamine hydrochloride melting at 149°–151° C.

Analysis: calculated: C, 42.36; H, 6.32; Cl, 27.78 found: C, 42.11; H, 6.18; Cl, 27.57.

Preparation 5

Preparation of 2-[2-(2-dimethylamino)ethyl-4-thiazolylmethylthio]ethylamine

A reaction mixture was prepared from 22.4 g. of N,N-dimethylcyanoacetamide, 21 ml. of liquid hydrogen sulfide and 1 ml. of triethylamine. The reaction mixture was placed in an autoclave and the autoclave shaken at about 55° C. for about 12 hours. The reaction mixture was taken from the autoclave and the volatile constituents removed by evaporation. Ethanol was added to the residue, thus producing a crystalline solid. The solid was filtered and the filter cake washed with cold ethanol. Twenty-one grams of 3-amino-3-thioxo-N,N-dimethylpropanamide were obtained melting at 111°–114° C. The compound had the following nmr (CDCl$_3$+DMSOd$_6$):$\delta$3.07 (doublet, 6H); 3.82 (singlet, 2H); 9.1 (very broad, 1H).

A reaction mixture was prepared from 21 g. of 3-amino-3-thioxo-N,N-dimethylpropanamide, 21 ml. of ethyl bromopyruvate and 200 ml. of ethanol. The reaction mixture was heated to refluxing temperature for 1.5 hours after which time the ethanol was removed by evaporation. A crystalline solid remained which was triturated with ethanol and again filtered. Recrystallization of the crude product from ethanol yielded 20.5 g. of ethyl 2-dimethylaminocarbonylmethylene-4-thiazolecarboxylate hydrobromide melting at about 150°–153° C. The compound had the following nmr (CDCl$_3$):$\delta$ 1.43 (triplet, 3H); 3.10 (doublet, 6H); 4.45 (quartet, 2H); 5.02 (singlet, 2H); 8.33 (singlet, 1H); 10.6 (singlet, 1H).

A solution was prepared from 20.5 g. of ethyl 2-dimethylaminocarbonylmethylene-4L-thiazolecarboxylate, hydrobromide, 50 ml. of ethanol and 50 ml. of water. One hundred twenty-seven ml. of 1N aqueous sodium hydroxide were added and the resulting solution stirred for about 24 hours at room temperature. The ethanol was then removed by evaporation. The aqueous layer was extracted with ether and the ether discarded. Sixty-three and one half ml. of 1N aqueous hydrochloric acid were then added. The acidic aqueous solution was chilled overnight and a crystalline solid which precipitated comprising 2-dimethylaminocarbonylmethylene-4-thiazolecarboxylic acid was separated by filtration. The filter cake was washed with a small amount of cold water. 7.85 g. of product were obtained melting at 187°–188° C. An additional 4.40 g. of 2-dimethylaminomethylcarbonylmethylene-4-thiazolecarboxylic acid were obtained from the mother liquor.

Analysis: calculated: C, 44.87; H, 4.70; N, 13.08; found: C, 44.60; H, 4.76; N, 12.87.

A suspension of 4.28 g. of 2-dimethylaminocarbonylmethylene-4-thiazolecarboxylic acid in 50 ml. of THF was kept at about 15° C. under a nitrogen atmosphere. 80 ml. of a 1M borane solution in THF were added. The reaction mixture was stirred for three hours at about 10° C. after which time it was cooled to 0° C. and 10 ml. of methanol were added in dropwise fashion. The reaction mixture was then allowed to remain overnight at room temperature. The volatile constituents were removed by evaporation in vacuo. Twenty ml. of methanol and 10 ml. of 6N aqueous hydrochloric acid were added to the residue. The resulting solution was heated to refluxing temperature on a steam bath for 1.5 hours. The methanol was then removed by evaporation and 4.5 g. of sodium bicarbonate were added to the remaining aqueous solution. Water was removed from this solution in vacuo and the solid residue triturated with ethanol. The ethanol was removed by evaporation. This trituration process was repeated twice using isopropanol. The residual solid was then extracted four times with boiling isopropanol. The isopropanol extracts were filtered and the isopropanol removed from the filtrate by evaporation. 4.1 g. of an oil comprising 2-(2-dimethylamino)ethyl-4-thiazolemethanol were obtained. The compound was purified using high-pressure liquid chromatography over silica with ethanol as the eluant. 0.9 g. of product were obtained having the following nmr (CDCl$_3$+DMSOd$_6$):δ 1.42 (singlet, 6H); 2.74-3.4 (overlapping triplets, 4H); 4.65 (singlet, 2H); 4.8 (broad, greater than 1H); 7.00 (singlet, 1H).

Following the procedure of Preparation 4, 2-(2-dimethylamino)ethyl-4-thiazolemethanol was converted to 2-(2L-dimethylamino)ethyl - 4 - thiazolemethylchloride hydrochloride with thionyl chloride. Next, the chloride hydrochloride was reacted with cysteamine hydrochloride to yield 2-[2-(2-dimethylamino)ethyl-4-thiazolyl-methylthio]ethylamine.

Mass spectrum: m/e 346;

In Flow Chart A above, compound I is a substituted aminothioacetamide hydrohalide of the structure

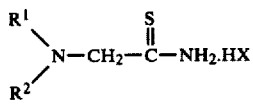

Where the substituting groups are alkyl, the compounds are known as, for example, dimethylaminothioacetamide, diethylaminothioacetamide, etc. and can be prepared by the method of *J. Org. Chem.*, (Russia), 6, 884 (1970) in English.

Illustrative preparations of other useful starting materials are given below.

Preparation 6

Morpholinothioacetamide

A reaction mixture was prepared from 203 ml. each of triethylamine and pyridine plus 63 g. of morpholinoacetonitrile. Hydrogen sulfide was bubbled through the heated, stirred reaction mixture for about 2.5 hours. Stirring was continued overnight at ambient temperature. The next day, H$_2$S was passed through the heated, stirred reaction mixture for an additional 1.5 hours. At this point, the solvents were evaporated in vacuo and the residue triturated with ether. The ether was discarded and the residue dissolved in ethanol. Crystalline morpholinothioacetamide formed in the above reaction precipitated and was separated by filtration. Treatment of the filtrate with alcoholic hydrogen chloride yielded morpholinothioacetamide hydrochloride melting in the range 64°-80° C. See also *J.A.C.S.*, 72, 2804 (1950).

Following the above procedure but using piperidinoacetonitrile in place of morpholinoacetonitrile, there was prepared piperidinothioacetamide hydrochloride melting at 166°-168° C., after recrystallization from ethylacetate. See also *Helv. Chim. Act.*, 43, 659 (1960).

Yield 35 g. from 62 g. of piperidinoacetonitrile starting material.

Following the above procedure using 100 g. of pyrrolidinoacetonitrile, there were obtained 68.4 g. of pyrrolidinothioacetamide hydrochloride (new) melting at about 195°-197° C.

Analysis calculated: C, 39.88; H, 7.25; N, 15.50; S, 17.74. Found: C, 39.66; H, 6.99; N, 15.76; S, 17.84.

Following the above procedure but using 49 g. of methylethylaminoacetonitrile, 200 ml. of triethylamine and 200 ml. of benzene, there was prepared N-methyl-N-ethylaminothioacetamide hydrochloride (new) melting at 115°-117° C.

The above procedures illustrate the preparation of one starting material from Flow Chart B [Formula V or Va (V when Z is S)] useful in preparing the compounds of this invention when both R$^1$ and R$^2$ are alkyl or when R$^1$ is H and R$^2$ alkyl. The other starting material used in Flow Chart B is a 5-substituted-4-pyrimidone (VI). Such compounds, where the leaving group Q is a nitroamino group, are conveniently prepared by reacting nitroguanidine with a compound of the formula:

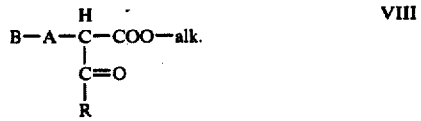

where alk, R, B and A have their previously assigned meaning. The esters of VIII in turn are prepared by acylating an ester of the formula B-A-CH$_2$COOalk on the α-carbon. This series of reactions is illustrated in Flow Chart H below wherein R is H, B is a 3-pyridyl group and A is methylene.

Flow Chart H

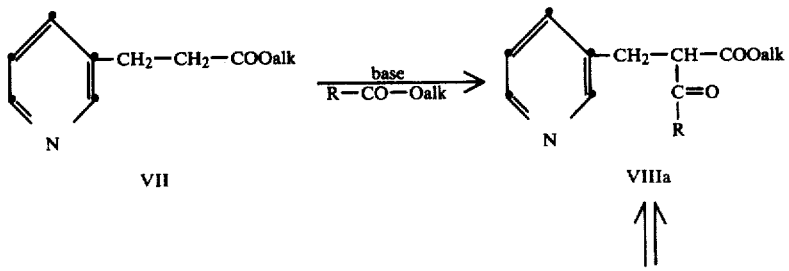

Flow Chart H

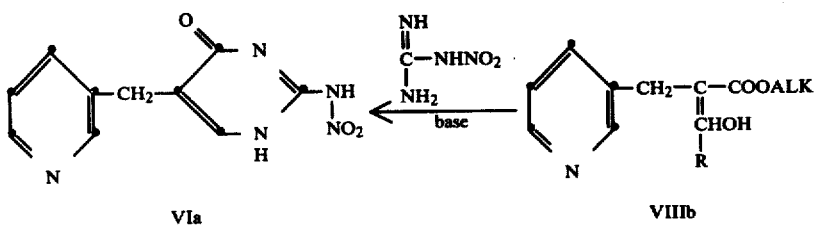

The pyridyl substituted acetate can be prepared from a 3-pyridylacrylic acid ester or from a 3-pyridylpropiolic acid ester by reduction. It will be apparent that condensation of the α-acylpropionate with S-methylisothiourea (or S-benzylisothiourea) would provide a 4-pyrimidone having a methylthio (or benzylthio) leaving group (Q in formula VI). In addition, U.S. Pat. No. 4,216,318 discloses specific procedure for the preparation of compounds according to VI wherein Q is lower alkylthio, halo(Cl, Br) or benzylthio, A is alkylene, R is H or methyl and B is pyridyl, methylpyridyl, quinolyl, thienyl or thiazolyl. Compounds in which B is furyl, methoxypyridyl, dialkylpyridyl or imidazolyl can be prepared similarly.

The following additional references are particularly valuable for giving directions for the preparation of 5-substituted-4-pyrimidones or 4-pyrimidinethiones containing a leaving group in the 2-position corresponding to the following formula.

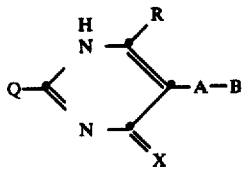

Belgian Pat. No. 877,899, EPO Pat. Nos. 3677, 7232, 51138, U.S. Pat. Nos. 4,154,834, 4,234,588, 4,255,428.

The above references plus the following illustrative preparations can either supply directly the pyrimidone intermediates of the above formula or the procedures disclosed therein or in the voluminous literature associated with pyrimidine chemistry can be readily adapted by one skilled in the art to provide any desired pyrimidone.

Preparation 7

Preparation of 2-methylmercapto-5-(6-methyl-3-pyridyl)oxy-4-pyrimidone.

A suspension of 5.5 g. of sodium hydride in 125 ml. of anhydrous dimethylformamide was prepared. 25.1 g. of 3-hydroxy-6-methylpyridine was added portionwise thereto. The consequent reaction mixture was stirred for about 1 hour and then cooled in an ice bath. 40.7 g. of ethyl bromoacetate in 20 ml. of ether were added thereto. The resulting reaction mixture was stirred at room temperature for about 3 days. A solid which precipitated was collected by filtration. The solvents were evaporated from the filtrate in vacuo, and the resulting residue dissolved in water. The aqueous solution was acidified by the addition of 19 ml. of 12N aqueous hydrochloric acid. The acidic aqueous layer was extracted several times with ether. The ether extracts were discarded. The acidic aqueous layer was then made basic by the addition of 55 ml. of 5N aqueous sodium hydroxide. An oil comprising ethyl (6-methyl-3-pyridyl)oxyacetate formed in the above reaction, separated and was extracted into either. The ether extract was washed with water and then dried. The ether was removed therefrom by evaporation yielding 11.7 g. of ethyl (6-methyl-3-pyridyl)oxyacetate as an oil.

Mass spectrum: m/e=195

A suspension of 2.85 g. of sodium hydride was prepared in 30 ml. of 1,2-dimethoxyethane. The suspension was cooled and stirred while a mixture containing 10.8 g. of ethyl formate and 18.6 g. of ethyl (6-methyl-3-pyridyloxy)acetate was added thereto. The consequent reaction mixture was stirred for about 1 day and then poured over ice water. The reaction mixture was then extracted several times with ether. The ether extracts were discarded. The remaining aqueous layer was acidified to a pH in the range 6–7 with 2N aqueous sulfuric acid. The resulting neutral layer was extracted with ether and the ether extract separated and dried. Evaporation of the ether yielded 10.5 g. of ethyl formyl-(6-methyl-3-pyridyloxy)acetate as a brown gum.

Mass spectrum: m/e=223.

13.2 g. of sodium were added to 400 ml. of anhydrous ethanol. After all of the sodium had reacted to form sodium ethoxide, a solution containing 23.7 g. of thiourea and 58.1 g. of ethyl formyl-(6-methyl-3-pyridyloxy)acetate in 360 ml. of ethanol was added. The consequent reaction mixture was heated to reflux temperature for about 16 hours and was then cooled to about 0° C. 44.4 g. of methyl iodide were added thereto in dropwise fashion. The reaction mixture was stirred at room temperature for about an additional 18 hours after which time the volatile components were removed by evaporation. The residue remaining was dissolved in water. The pH of the resulting aqueous solution was adjusted to a pH in the range of 6–7 with 1N aqueous hydrochloric acid. A solid comprising 2-methylthio-5-(6-methyl-3-pyridyloxy)-4-pyrimidone precipitated and was separated by filtration. The filter cake was washed with water and ether. 34.3 g. of 2-methylmercapto-5-(4-methyl-3-pyridyl)oxy-4-pyrimidone were obtained melting at 162°–164° C.

Preparation 8

Preparation of 2-methylthio-5-[2-(3-pyridyl)ethyl]-4-pyrimidone

A suspension of 2.53 g. of sodium hydride in 35 ml. of anhydrous dimethyl formamide was prepared. The suspension was cooled to about 0° C. with stirring. Next, a mixture of 9.56 g. of ethyl formate and 19 g. of ethyl 4-(3-pyridyl)butyrate were added. The consequent reaction mixture was stirred at about 0° C. for 1 additional hour and then at room temperature for about 3 days. The reaction mixture was acidified with 2N aqueous hydrochloric acid and the acidic aqueous solution evaporated to a very small volume in vacuo. The acidity of the solution was adjusted to pH=6 by the addition of solid potassium carbonate. The neutral aqueous layer was then extracted with ether. The ether layer was separated and dried. Evaporation of the ether yielded 16.4 g. of ethyl 2-formyl-4-(3-pyridyl)butyrate (formed in the above reaction) as an orange oil.

Mass spectrum: m/e=222 (P+1)

About 3.75 g. of sodium were added to 220 ml. of anhydrous ethanol thus forming a solution of sodium ethoxide in ethanol. After all of the sodium had reacted, a mixture of 6.73 g. of thiourea and 16.35 g. of ethyl 2-formyl-4-(3-pyridyl)butyrate were added. This reaction mixture was heated to refluxing temperature for 21 hours after which time the solvent was removed by evaporation. The resulting residue was dissolved in water and the aqueous layer extracted successively with ether and chloroform. The pH of the aqueous layer was then adjusted to about 7 with 12N aqueous hydrochloric acid. A yellow solid comprising 5-[2-(3-pyridyl)ethyl]-2-thiouracil precipitated and was collected by filtration. The filter cake was washed with water and a small amount of ether to yield 10.5 g. of the uracil melting at 254°-258° C. with decomposition.

Mass spectrum: m/e=233

2.18 g. of sodium were added to 130 ml. of anhydrous ethanol thus forming a solution of sodium ethoxide in ethanol. 10 g. of 5-[2-(3-pyridyl)ethyl]-2-thiouracil were added and the resulting mixture was stirred for about 1.5 hours (thus forming the sodium salt of the thiol group) and was then cooled to about 0° C. A solution of 7.1 g. of methyl iodide and 5 ml. of ethanol was next added in dropwise fashion to the chilled reaction mixture with stirring. The stirring was continued for an additional 3.5 hours while maintaining the temperature at 0° C. The reaction mixture was then allowed to warm up to room temperature, at which temperature it was stirred for an additional hour. The solvent was removed by evaporation in vacuo. The resulting residue was dissolved in water and the aqueous solution neutralized with 10% aqueous hydrochloric acid. A yellow solid precipitated and was collected by filtration. The filter cake was washed with water plus a small quantity of ether. 9.0 g. of 2-methylthio-5-[2-(3-pyridyl)ethyl]-4-pyrimidone melting at 191°-192° C. were obtained.

Following the above procedure, 3.03 g. of sodium were suspended in anhydrous ether in a nitrogen atmosphere. 5.93 g. of ethyl formate plus 14.1 g. of ethyl 3-pyridylmethoxyacetate were added. The product of the reaction, ethyl formyl-(3-pyridylmethoxy)acetate as the sodium salt, was suspended in 175 ml. of ethanol and 5.8 g. of thiourea were added. The product of this reaction, 5-(3-pyridylmethoxy)-2-thiouracil, melted at 243°-245° C.; weight=10.4 g. 9.9 g. of the uracil were slurried in 80 ml. of ethanol. A solution containing 1.78 g. of sodium hydroxide and 38 ml. of water was added followed by 4.86 g. of methyl iodide. 1.46 g. of 2-methylthio-5-(3-pyridyl)methoxy-4-pyrimidone were obtained melting at 186°-187° C.

Preparation 9

Preparation of 2-nitroamino-6-methyl-5-(3-pyridyl)methyl-4-pyrimidone

A solution of sodium methoxide in methanol was prepared by adding 1.8 g. of sodium to 75 ml. of anhydrous methanol. 7.04 g. of dried nitroguanidine were added thereto under a positive nitrogen atmosphere. This mixture was heated at reflux temperature for about one-half hour, after which time 15 g. of ethyl 2-(3-pyridyl)methylacetoacetate (prepared according to the procedure of U.S. Pat. No. 4,216,318) were added thereto and the resulting reaction mixture was heated at reflux temperature for about 19 hours. The volatile constituents were removed by evaporation and the resulting residue dissolved in water. The aqueous solution was extracted 4 times with chloroform and the chloroform extracts were discarded. The aqueous layer was then made slightly acid (pH=6) by the addition of 5N aqueous hydrochloric acid. A solid comprising 2-nitroamino-6-methyl-5-(3-pyridyl)methyl-4-pyrimidone formed in the above reaction precipitated and was collected by filtration. The filter cake was washed with water and dried. 7.1 g. of product melting at 231°-233° C. were obtained. Recrystallization of the filter cake from a mixture of dimethylformamide and methanol yielded 4.8 g. of 2-nitroamino-6-methyl-5-(3-pyridyl)methyl-4-pyrimidone melting at 238°-239° C.

Preparation 10

Preparation of 2-methylthio-5-(3-pyridyl)methyl-4-pyrimidinethione

A suspension was prepared from 1.2 g. of sodium hydride in 40 ml. of anhydrous DMF. 11.7 g. of 2-methylthio-5-(3-pyridyl)methyl-4-pyrimidone were added thereto under a positive nitrogen atmosphere. The reaction mixture was heated with stirring until all of the suspended hydride had disappeared. Next, 7.4 g. of dimethylthiocarbamoyl chloride were added in portions while maintaining the reaction mixture at room temperature. After all of the carbamoyl chloride had been added, the reaction mixture was heated to 75° C. and stirred at that temperature for 3 hours. The reaction mixture was then poured into 400 ml. of 1% aqueous potassium hydroxide. O-[2-methylthio-5-(3-pyridyl)methyl-4-pyrimidyl]dimethylthiocarbamate formed in the above reaction precipitated and was separated by filtration. The filter cake was washed with water and ether. Recrystallization of the filter cake from isopropanol yielded 3.22 g. of O-[2-methylthio-5-(3-pyridyl)methyl-4-pyrimidyl]dimethylthiocarbamate melting at 122°-123° C.

2.67 g. of the above carbamate were heated with stirring at 180° C. for one-half hour, and were then taken up in a mixture of 10 ml. of methanol and 10 ml. of 1N aqueous sodium hydroxide. The water and methanol were removed by evaporation and the resulting residue dissolved in water. The cooled solution was neutralized with 10 ml. of 1N aqueous hydrochloric acid. 2-Methylthio-5-(3-pyridyl)methyl-4-pyrimidinethione formed in the above reaction precipitated and separated by filtration. The filter cake was washed with water. The compound thus prepared melted at 211°-213° C. after drying.

Analysis Calculated: C, 52.98; H, 4.45; N, 16.85; Found: C, 52.74; H, 4.16; N, 17.14.

Preparation 11

Preparation of 2-nitroamino-5-(4-pyridyl)methyl-4-pyrimidone

About 1.77 g. of sodium were dissolved in 75 ml. of anhydrous methanol under a positive nitrogen atmosphere. The sodium methoxide in methanol solution was cooled and 7.28 g. of dried nitroguanidine added thereto. The reaction mixture was heated to reflux temperature briefly after which time 14.5 g. of ethyl 2-formyl-3-(4-pyridyl)propionate (prepared by the method of U.S. Pat. No. 4,216,318) were added thereto. This reaction mixture was then heated to refluxing temperature for about 19 hours. Volatile constituents were removed by evaporation and water was added to the residue. The aqueous mixture was extracted 3 times with chloroform and the chloroform extracts discarded. The aqueous solution was then chilled to about 0° C. and 15.4 ml. of 5N aqueous hydrochloric acid added. 2-Nitroamino-5-(4-pyridyl)methyl-4-pyrimidone formed in the above reaction precipitated and the precipitate was collected by filtration. The filter cake was washed with water and dried. 9.9 g. of product were obtained melting at about 228°–229° C.

Following the above procedure, sodium methoxide and nitroquanidine were heated to form the sodium salt. 17.8 g. of ethyl 2-formyl-3-(2-pyridyl)propionate (prepared as described in U.S. Pat. No. 4,216,318) were added thereto. 2-Nitroamino-5-(2-pyridyl)methyl-4-pyrimidone was isolated and purified by the above procedure. The compound melted at about 195°–197° C. (yield = 17.2 g.).

The compounds of this invention are potent $H_2$ receptor antagonists and thus potential anti-ulcer agents. The relation of the $H_2$ receptors to mammalian gastric secrection is described in an article by Black et al. *Nature*, 236, 385 (1972).

The following assay for $H_2$ receptor blocking activity was employed. Female albino rats are treated with estrone 24 hours prior to the initiation of the experiment. The rats are sacrificed and the uterine horns removed therefrom and suspended at ambient temperature in isolated organ baths containing De Jalon's solution. After equilibration, the uterine strips are exposed to 50 millimole aqueous potassium chloride, which produces a sustained contraction. When the uterus is so contracted, histamine produces a dosedependent $H_2$ receptor-mediated relaxation. A control dose-response curve to histamine is constructed on each tissue. Following thorough washout of the histamine after obtaining the control dose-response curve, each antagonist (a compound of this invention) is added for 30 minutes at a concentration of $10^{-5}$ molar. The uterine strips are then contracted with aqueous potassium chloride in the presence of the antagonist and a second dose-response curve to histamine obtained. In the presence of a competitive antagonist, the dose-response curve to histamine is shifted in parallel to the right with no depression of the maximum relative to the control curve. The dose ratio (DR) is calculated for each concentration of antagonist by dividing the $ED_{50}$ of histamine in the presence of the competitive antagonist by the control $ED_{50}$ for histamine. The dissociation constant ($K_B$) of the antagonist is calculated from the dose-ratios by the following equation:

$K_B = [\text{antagonist}]/(DR-1)$

Cimetidine is included as an internal standard.

Results of the above assay carried out on selected compounds of this invention are set forth in Table 1.

In the table, column 1 gives the name of the compound under test and column 2, the $-\log K_b$ value for that compound.

TABLE 1

| name | $-\log k_b$ |
| --- | --- |
| 2-[2-(2-dimethylaminomethyl-4- | 8.96 |

TABLE 1-continued

| name | $-\log k_b$ |
| --- | --- |
| thiazolylmethylthio)ethyl]amino-5-(3-pyridyl)methyl-4-pyrimidone | |
| 2-[2-(2-dimethylaminomethyl-4-thiazolylmethylthio)ethyl]amino-5-[5-(1,3-benzodioxolyl)]methyl-4-pyrimidone | 8.36 |
| 2-[2-(2-dimethylaminomethyl-4-thiazolylmethylthio)ethyl]amino-5-(6-methyl-3-pyridyl)methyl-4-pyrimidone | 7.95 |
| 2-[2-(2-dimethylaminomethyl-4-thiazolylmethylthio)ethyl]amino-5-(4-pyridyl)methyl-4-pyrimidone | 7.89 |
| 2-[2-(2-dimethylaminomethyl-4-thiazolylmethylthio)ethyl]amino-5-(2-pyridyl)methyl-4-pyrimidone | 7.76 |
| 2-[2-(2-Dimethylaminomethyl-4-thiazolylmethylthio)ethyl]amino-5-(6-methoxy-3-pyridyl)methyl-4-pyrimidone | 7.22 |
| 2-[2-(2-Dimethylaminomethyl-4-thiazolylmethylthio)ethyl]amino-5-(5,6-dimethyl-3-pyridyl)methyl-4-pyrimidone | 8.41 |

A second assay for $H_2$ receptor blocking activity employs the isolated bullfrog gastric mucosa—see Warrick and Lin, *Communications in Chem. Pathology and Pharmacology*, 13, 149 (1976). The assay is carried out as follows: The gastric mucosa of the bullfrog (*Rana catesbeiana*) is separated from the musculature of the stomach and placed between a pair of Ussing chambers made of lucite. The chambers are filled with frog Ringer solution and acid secretion is stimulated by addition of histamine to the serosal side of the mucosa at a final concentration of $10^{-5}M$. Acid output is automatically titrated to pH 4.5. After steady response to $10^{-5}M$ of histamine is established, the antagonist (a compound of this invention) is added to the serosal chamber and the maximal inhibition by each concentration of the $H_2$-antagonist is recorded. From the dose-response curve, the $ED_{50}$ of the drug is calculated. Results obtained with compounds of this invention in this assay are set forth in Table 2.

In Table 2, column 1 gives the substituent at 6 in the pyrimidone ring, column 2 the "B" group (see formula at the head of the Table), and column 3 the molar $ED_{50}$.

TABLE 2

| R | B | $ED_{50}$ in moles |
| --- | --- | --- |
| H | 3-pyridyl | $1.15 \times 10^{-7}$ |
| H | 6-methyl-3-pyridyl | $1.35 \times 10^{-6}$ |
| H | 6-methoxy-3-pyridyl | $1.26 \times 10^{-5}$ |
| H | 6-hydroxy-3-pyridyl | $2.52 \times 10^{-7}$ |
| H | 5-(1,3-benzodioxolyl) | $1.11 \times 10^{-5}$ |
| H | 4-pyridyl | $1.96 \times 10^{-7}$ |
| H | 2-pyridyl | $1.63 \times 10^{-7}$ |
| H | 5,6-dimethyl-3-pyridyl | $2.35 \times 10^{-6}$ |
| $CH_3$ | 3-pyridyl | $2.00 \times 10^{-6}$ |
| H | 2-methoxy-4-pyridyl | $3.00 \times 10^{-6}$ |

TABLE 2-continued

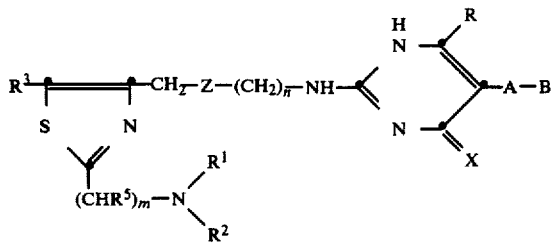

| R | B | $ED_{50}$ in moles |
|---|---|---|
| H | 2-hydroxy-4-pyridyl | $6.03 \times 10^{-7}$ |

An in vivo assay for the antisecretory action of drugs on acid secretion utilizes gastric fistula dogs with a vagally innervated gastric fistula and vagally denervated Heidenthain pouch. A steady-state gastric secretion is produced by the iv infusion of histamine. The antisecretory drugs under test are given either intravenously by infusion over a 30 minute period or orally 75 min. prior to collection of gastric secretion from the fistula. In this assay, 2-[2-(2-dimethylaminomethyl-4-thiazolylmethylthio)ethyl]amino-5-(3-pyridyl)methyl-4-pyrimidone was 11X cimetidine by the iv route and 14X cimetidine orally. The 6-methyl-2-pyridyl analog was 14.4X cimetidine intravenously.

According to these and other tests, the compounds of this invention are more active than cimetidine, particularly when given orally. The compounds are also apparently much longer acting than cimetidine since recovery from an effective dose of 2-[2-(2-dimethylaminomethyl-4-thiazolylmethylthio)ethyl]amino-5-(3-pyridyl)methyl-4-pyrimidone is about 25% after 3-4 hours at which time cimetidine shows about a 50% recovering of acid secretions.

It is an advantage of the compounds of this invention that they also possess H-1 histamine receptor inhibitory action, and thus can effect those physiological states which are produced by a mixture of $H_1$ and $H_2$ histamine receptor stimulation.

In utilizing the compounds of this invention as antisecretory agents, either the parenteral or oral route of administration may be employed. For oral dosage, a suitable quantity of a free base of one of the preferred compounds of this invention or a pharmaceutically-acceptable salt thereof formed with a non-toxic acid such as a hydrochloride salt is mixed with one or more conventional excipients such as starch and the mixture placed in telescoping gelatin capsules or compressed into tablets, each containing from 10-90 mg. of active ingredients per dosage unit. The tablets may be scored if lower or divided dosages are to be used. For parenteral administration via an iv infusion, an isotonic solution of a salt is preferably employed although a soluble free base is also useful in isotonic preparations. However, the oral route of administration is preferred.

Because of the high oral absorption and longer duration of action of the compounds of this invention, it is believed that oral administration of about 40-90 mg. once a day will suffice to control acid secretion in ulcer patients and thus alleviate ulcer symptoms. However, if a multiple dose regimen is desired, the daily dose can be subdivided, for example, into 10-25 mg four times a day or 20-45 mg twice a day. As would be expected, higher dosages would be required for compounds not as active as my preferred compounds, such higher dosages being in the range 120-360 mg./day. The preferred oral dosage range is about 0.5-1.5 mg./kg./day of mammalian body weight for the more active drugs.

I claim:

1. A compound of the formula

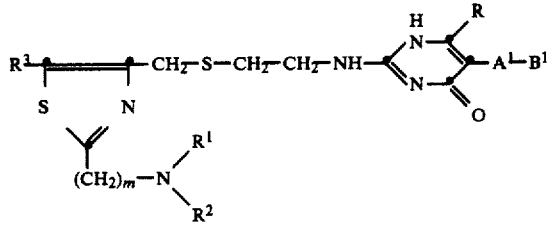

wherein each of R, $R^1$, $R^2$ and $R^3$ are individually H or $(C_1-C_3)$ alkyl, $R^1$ can additionally be benzyl or benzoyl when $R^2$ is $(C_1-C_3)$ alkyl, and when taken together with the nitrogen to which they are attached, $R^1$ and $R^2$ represent a saturated 5-7 membered heterocyclic ring containing permissibly a second hetero atom selected from the group consisting of O and N; except that only one of $R^1$ and $R^2$ can be H when Z is $CH_2$;

Z is O, S or $CH_2$;

X is S or O;

n is 2 or 3 when Z is O or S and n is 1, 2 or 3 when Z is $CH_2$;

$R^5$ is H or $CH_3$;

m is 1, 2 or 3;

A is $(C_1-C_5)$ alkylene or $(CH_2)_qX(CH_2)_p$ wherein q and p are individually 0, 1, 2 or 3 and the sum of q plus p is 0-4, and B is H, $CH_3$, $(C_3-C_6)$cycloalkyl, naphthyl, pyridyl, $(C_1-C_3)$alkylpyridyl, di$(C_1-C_3)$alkylpyridyl, hydroxypyridyl, $(C_1-C_3)$alkyloxypyridyl, 5-(1,3-benzodioxolyl), 6-(2,3-dihydro-1,4-benzodioxinyl), phenyl permissibly substituted with methylenedioxy or 1 or 2 (same or different) $(C_1-C_3)$alkyl, $(C_1-C_3)$alkyloxy, halo, OH, benzyloxy, $CF_3$, $(C_1-C_3)$alkyl-O-$(C_1-C_3)$alkylene, phenoxy or di[(-$C_1-C_3$)alkyl]amino$(C_1-C_3)$alkylene groups; and pharmaceutically-acceptable acid-addition salts thereof.

2. A compound of the formula

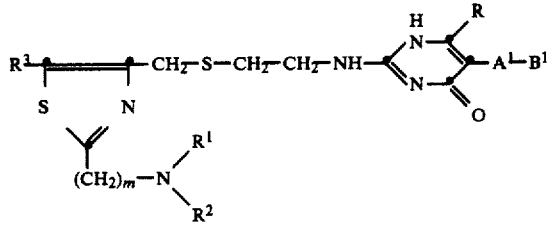

wherein R, $R^1$, $R^2$ and $R^3$ are H or $(C_1-C_3)$alkyl, $R^1$ is benzyl when $R^2$ is $(C_1-C_3)$alkyl, m is 1-3, $A^1$ is $(C_1-C_5)$alkylene and $B^1$ is pyridyl, phenyl, 5-(1,3-benzodioxolyl), 6-(2,3-dihydro-1,4-benzodioxinyl), $(C_1-C_3)$alkylpyridyl, di$(C_1-C_3)$alkylpyridyl, hydroxypyridyl or $(C_1-C_3)$alkyloxypyridyl.

3. A thiazole derivative as claimed in claim 1 wherein $R^1$ and $R^2$ individually represent H or $(C_1-C_3)$alkyl, $R^1$ may additionally represent benzyl when $R^2$ is $(C_1-C_3)$alkyl or $R^1$ and $R^2$ taken together with the adjacent nitrogen atom represent a piperidino, pyrrolidino or morpholino group, provided that only one of $R^1$ and $R^2$ can be hydrogen when Z is $CH_2$; $R^3$ is hydrogen or ($C_1-C_3$)alkyl; $R^5$ is hydrogen or methyl; A is ($C_1-C_5$)alkylene, B is pyridyl permissibly substituted with OH, ($C_1-C_3$)alkyloxy or one or two ($C_1-C_3$)alkyl groups; and pharmaceutically-acceptable, acid-addition salts thereof.

4. A thiazole derivative as claimed in claim 1, wherein Z is sulfur.

5. A thiazole derivative as claimed in claim 1, wherein n is 2.

6. A thiazole derivative as claimed in claim 1, wherein $R^3$ is hydrogen.

7. A thiazole derivative as claimed in claim 1, wherein $R^5$ is hydrogen.

8. A thiazole derivative as claimed in claim 1, wherein m is 1.

9. A thiazole derivative as claimed in claim 1, wherein $R^1$ and $R^2$ are methyl.

10. A thiazole derivative as claimed in claim 8, wherein the $-(CHR^5)_mNR^1R^2$ group is dimethylaminomethyl.

11. A thiazole derivative as claimed in claim 1, wherein A is $CH_2$.

12. A thiazole derivative as claimed in claim 1, wherein B is pyridyl, hydroxypyridyl, ($C_1-C_3$)alkyloxypyridyl, ($C_1-C_3$)alkylpyridyl or di($C_1-C_3$)alkylpyridyl.

13. A compound according to claim 12 in which B is pyridyl.

14. A thiazole derivative as claimed in claim 12, wherein R is H.

15. A compound according to claim 1 in which R, $R^3$ and $R^5$ are H, $R^1$ and $R^2$ are independently H or ($C_1-C_3$)alkyl, X is O, n is 2 or 3, A is methylene and B is pyridyl or pyridyl substituted with 1 or 2 members of the group OH, ($C_1-C_3$)alkyl or ($C_1-C_3$)alkyloxy.

16. A compound according to claim 2 in which $B^1$ is 3-pyridyl, hydroxy-substituted 3-pyridyl, methyl-substituted 3-pyridyl or dimethyl-substituted 3-pyridyl.

17. A compound according to claim 1 in which $R^1$ is H or methyl and $R^2$ is methyl.

18. A compound according to claim 1 in which the hetero ring formed by $R^1$, $R^2$ and the nitrogen to which they are attached is piperidino, pyrrolidino or morpholino.

19. A compound according to claim 1, said compound being 2-[2-(2-dimethylaminomethyl-4-thiazolylmethylthio)ethyl]amino-5-(3-pyridyl)methyl-4-pyrimidone.

20. A compound according to claim 1, said compound being 2-[2-dimethylaminomethyl-4-thiazolylmethylthio)ethyl]amino)-5-[5-(1,3-benzodioxolyl)]methyl-4-pyrimidone.

21. A compound according to claim 1, said compound being 2-[2-(2-dimethylaminomethyl-4-thiazolylmethylthio)ethyl]amino-5-(6-methyl-3-pyridyl)methyl-4-pyrimidone.

22. A compound according to claim 1, said compound being 2-[2-(2-dimethylaminomethyl-4-thiazolylmethylthio)ethyl]amino-5-(4-pyridylmethyl)-4-pyrimidone.

23. A compound according to claim 1, said compound being 2-[2-(2-dimethylaminomethyl-4-thiazolylmethylthio)ethyl]amino-5-(2-pyridyl)methyl-4-pyrimidone.

24. A compound according to claim 1, said compound being 2-[2-(2-dimethylaminomethyl-4-thiazolylmethylthio)ethyl]amino-5-(2-methoxy-4-pyridyl)methyl-4-pyrimidone.

25. A compound according to claim 1 said compound being 2-[2-(2-dimethylaminomethyl-4-thiazolylmethylthio)ethyl]amino-5-(5,6-dimethyl-3-pyridyl)methyl-4-pyrimidone.

26. A pharmaceutical formulation in unit dosage form adapted for oral administration to achieve an antisecretory effect comprising, per dosage unit, an antisecretorially-effective amount of a compound of claim 1 plus one or more pharmaceutical excipients.

27. A pharmaceutical formulation according to claim 26 containing from 10–360 mg. of active drug per dosage unit.

28. A pharmaceutical formulation according to claim 26 in which the active antisecretory drug is 2-[2-(2-dimethylaminomethyl-4-thiazolylmethylthio)ethyl]amino-5-(3-pyridyl)methyl-4-pyrimidone.

29. A pharmaceutical formulation in unit dosage form adapted for oral administration to achieve an antisecretory effect comprising, per dosage unit, an antisecretorially-effective amount of a compound according to claim 2 plus one or more pharmaceutical excipients.

30. A method for inhibiting gastric acid secretion in mammals which comprises administering to a mammal whose gastric acid secretion is excessive and who is in need of treatment an antisecretorially-effective amount of a compound according to claim 1.

31. A method according to claim 30 in which from 40–360 mg. of drug per day are administered orally to humans.

32. A method according to claim 30 in which the oral daily dose is from 0.5–4.8 mg./kg. of mammalian body weight.

33. A method according to claim 30 in which 2-[2-(2-dimethylaminomethyl-4-thiazolylmethylthio)ethyl]amino)-5-(3-pyridyl)methyl-4-pyrimidone is the antisecretorially effective drug.

34. A method according to claim 30 in which 2-[2-(2-dimethylaminomethyl-4-thiazolylmethylthio)ethyl]amino-5-(2-methoxy-4-pyridyl)methyl-4-pyrimidone is the antisecretorially effective drug.

35. A method according to claim 30 in which 2-[2-(2-dimethylaminomethyl-4-thiazolylmethylthio)ethyl]amino-5-(4-pyridyl)methyl-4-pyrimidone is the antisecretorially effective drug.

36. A method according to claim 30 in which 2-[2-(2-dimethylaminomethyl-4-thiazolylmethylthio)ethyl]amino-5-(2-pyridyl)methyl-4-pyrimidone is the antisecretorially effective drug.

37. A method according to claim 30 in which 2-[2-(2-dimethylaminomethyl-4-thiazolylmethylthio)ethyl]amino-5-(6-methyl-3-pyridyl)methyl-4-pyrimidone is the antisecretorially-effective drug.

38. A method according to claim 30 in which 2-[2-(2-dimethylaminomethyl-4-thiazolylmethylthio)ethyl]amino-5-(5,6-dimethyl-3-pyridyl)methyl-4-pyrimidone is the antisecretorially-effective drug.

39. A method for inhibiting gastric acid secretion in mammals which comprises administering to a mammal whose gastric acid secretion is excessive and who is in need of treatment an antisecretorially-effective amount of a compound according to claim 2.

40. A method of inhibiting H-2 histamine receptors which comprises administering to an animal an amount effective to inhibit said receptors of a compound according to claim 1.

41. A compound of the formula

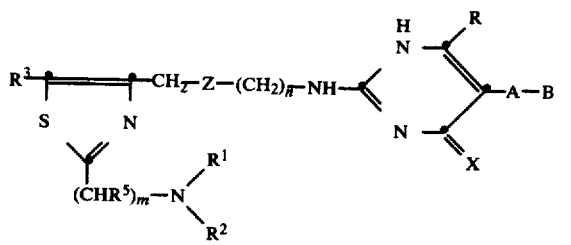

wherein each of R, $R^1$, $R^2$ and $R^3$ are individually H or ($C_1$–$C_3$) alkyl, $R^1$ can additionally be benzyl or benzoyl when $R^2$ is ($C_1$–$C_3$) alkyl, and when taken together with the nitrogen to which they are attached, $R^1$ and $R^2$ represent a saturated 5–7 membered heterocyclic ring containing permissibly a second hetero atom selected from the group consisting of O and N; except that only one of $R^1$ and $R^2$ can be H when Z is $CH_2$;

Z is O, S or $CH_2$;

X is S or O;

n is 2 or 3 when Z is O or S and n is 1, 2 or 3 when Z is $CH_2$;

$R^5$ is H or $CH_3$;

m is 1, 2 or 3;

A is ($C_1$–$C_5$) alkylene or $(CH_2)_q X(CH_2)_p$ wherein q and p are individually 0, 1, 2 or 3 and the sum of q plus p is 0–4, and B is H, $CH_3$, ($C_3$–$C_6$)cycloalkyl, naphthyl, pyridyl, ($C_1$–$C_3$)alkylpyridyl, di($C_1$–$C_3$)alkylpyridyl, hydroxypyridyl, ($C_1$–$C_3$)alkyloxypyridyl, imidazolyl, furyl, thienyl, thiazolyl, tetrahydrofuryl, 5-(1,3-benzodioxolyl), 6-(2,3-dihydro-1,4-benzodioxinyl), phenyl permissibly substituted with methylenedioxy or 1 or 2 (same or different) ($C_1$–$C_3$)alkyl, ($C_1$–$C_3$)alkyloxy, halo, OH, benzyloxy, $CF_3$, ($C_1$–$C_3$)alkyl-O-($C_1$–$C_3$)alkylene, phenoxy or di[($C_1$–$C_3$)alkyl]amino($C_1$–$C_3$)alkylene groups; and pharmaceutically-acceptable acid-addition salts thereof.

42. A compound of the formula

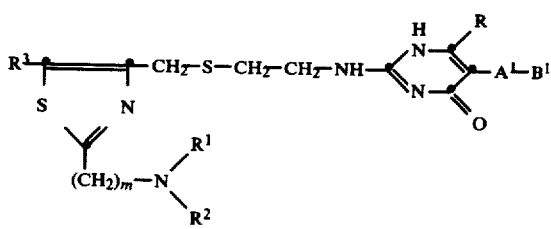

wherein R, $R^1$, $R^2$ and $R^3$ are H or ($C_1$–$C_3$)alkyl, $R^1$ is benzyl when $R^2$ is ($C_1$–$C_3$)alkyl, m is 1–3, $A^1$ is ($C_1$–$C_5$-)alkylene and $B^1$ is furyl, thienyl, imidazolyl, thiazolyl or tetrahydrofuryl.

43. A compound according to claim 42 in which R and $R^3$ are H, R and $R^2$ are methyl, $A^1$ is methylene and $B^1$ is thiazolyl, furyl, thienyl, imidazolyl or tetrahydrofuryl.

44. A compound according to claim 41, said compound being 2-[2-(2-dimethylaminomethyl-4-thiazolylmethylthio)ethyl]amino-5-(4-imidazolyl)methyl-4-pyrimidone.

45. A compound according to claim 41, said compound being 2-[2-(2-dimethylaminomethyl-4-thiazolylmethylthio)ethyl]amino-5-(2-furyl)methyl-4-pyrimidone.

46. A compound according to claim 41 said compound being 2-[2-(2-dimethylaminomethyl-4-thiazolylmethylthio)ethyl]amino-5-(2-thiazolyl)methyl-4-pyrimidone.

47. A pharmaceutical formulation in unit dosage form adapted for oral administration to achieve an antisecretory effect comprising, per dosage unit, an antisecretorially-effective amount of a compound of claim 41 plus one or more pharmaceutical excipients.

48. A pharmaceutical formulation in unit dosage form adapted for oral administration to achieve an antisecretory effect comprising, per dosage unit, an antisecretorially-effective amount of a compound according to claim 42 plus one or more pharmaceutical excipients.

49. A method for inhibiting gastric acid secretion in mammals which comprises administering to a mammal whose gastric acid secretion is excessive and who is in need of treatment an antisecretorially-effective amount of a compound according to claim 41.

50. A method for inhibiting gastric acid secretion in mammals which comprises administering to a mammal whose gastric acid secretion is excessive and who is in need of treatment an antisecretorially-effective amount of a compound according to claim 42.

51. A method of inhibiting H-2 histamine receptors which comprises administering to a mammal an amount effective to inhibit said receptors of a compound according to claim 41.

52. A method of inhibiting H-1 histamine receptors which comprises administering to a mammal an amount effective to inhibit said receptors of a compound according to claim 41.

53. A method of inhibiting both H-1 and H-2 receptors which comprises administering to a mammal an amount effective to inhibit said receptors of a compound according to claim 41.

54. A compound according to claim 1, said compound being 2-[2-(2-dimethylaminomethyl-4-thiazolylmethylthio)ethyl]amino-5-(2-methyl-4-pyridyl)methyl-4-pyrimidone.

* * * * *